United States Patent
Stordeur et al.

(10) Patent No.: US 7,700,276 B2
(45) Date of Patent: Apr. 20, 2010

(54) DEVICE, KIT AND METHOD FOR PULSING BIOLOGICAL SAMPLES WITH AN AGENT AND STABILISING THE SAMPLE SO PULSED

(75) Inventors: Patrick Stordeur, Brussels (BE); Michel Goldman, Brussels (BE)

(73) Assignee: Universite Libre de Bruxelles, Bruxelles (BE)

( * ) Notice: Subject to any disclaimer, the term of this patent is extended or adjusted under 35 U.S.C. 154(b) by 440 days.

(21) Appl. No.: 10/563,503

(22) PCT Filed: Jul. 10, 2003

(86) PCT No.: PCT/EP03/07453

§ 371 (c)(1), (2), (4) Date: Mar. 2, 2006

(87) PCT Pub. No.: WO2005/005044

PCT Pub. Date: Jan. 20, 2005

(65) Prior Publication Data

US 2007/0065825 A1    Mar. 22, 2007

(51) Int. Cl.
- C12Q 1/68 (2006.01)
- G01N 33/53 (2006.01)
- C12M 1/00 (2006.01)
- C12M 1/34 (2006.01)
- C12M 1/33 (2006.01)
- C07H 21/00 (2006.01)
- C07H 21/02 (2006.01)
- C07H 21/04 (2006.01)
- C07K 1/00 (2006.01)
- C07K 14/00 (2006.01)
- C07K 17/00 (2006.01)

(52) U.S. Cl. .................. 435/6; 435/7.1; 435/283.1; 435/287.2; 435/306.1; 536/22.1; 536/23.1; 536/24.3; 530/350

(58) Field of Classification Search .......... 435/6, 435/7.1, 283.1, 287.2, 306.1; 536/23.1, 24.3; 536/22.1; 530/350

See application file for complete search history.

(56) References Cited

U.S. PATENT DOCUMENTS

| | | | |
|---|---|---|---|
| 5,114,858 A | * | 5/1992 | Williams et al. ............ 435/270 |
| 5,362,654 A | | 11/1994 | Pouletty |
| 5,527,669 A | * | 6/1996 | Resnick et al. ................ 435/5 |
| 5,710,041 A | | 1/1998 | Moorman et al. |
| 6,255,478 B1 | | 7/2001 | Komai et al. |
| 6,281,008 B1 | * | 8/2001 | Komai et al. ............ 435/306.1 |
| 6,428,962 B1 | * | 8/2002 | Naegele ....................... 435/6 |
| 6,602,718 B1 | * | 8/2003 | Augello et al. ............. 436/176 |
| 6,776,959 B1 | * | 8/2004 | Helftenbein ................ 422/50 |
| 6,793,892 B1 | * | 9/2004 | Niermann ................... 422/101 |
| 7,283,371 B1 | * | 10/2007 | Grouell et al. .............. 361/741 |
| 2002/0064484 A1 | * | 5/2002 | Lin et al. .................... 422/101 |
| 2002/0182718 A1 | | 12/2002 | Malmquist |
| 2003/0108447 A1 | | 6/2003 | Yokoi et al. |
| 2003/0181868 A1 | * | 9/2003 | Swenson ..................... 604/263 |
| 2004/0161788 A1 | * | 8/2004 | Chen et al. .................... 435/6 |
| 2004/0256331 A1 | | 12/2004 | Arking et al. |
| 2005/0019750 A1 | | 1/2005 | Brem |
| 2008/0153078 A1 | | 6/2008 | Braman et al. |

FOREIGN PATENT DOCUMENTS

| | | |
|---|---|---|
| EP | 1 300 465 | 4/2003 |
| JP | 2001-194365 | 7/2001 |
| WO | WO 2005/014173 | 2/2005 |
| WO | WO 2007/070740 | 6/2007 |
| WO | WO 2008/067215 | 6/2009 |

OTHER PUBLICATIONS

Gene Characterization Kits ; The Stratagene Catalog p. 39 (1988).*
Product description of High Pure RNA Isolation Kit found at www.roche-applied-science.com, pp. 1-8.*
Rainen, et al. "Stabilization of mRNA Expression in Whole Blood Samples," *Clinical Chemistry*, vol. 48, No. 11, pp. 183-1890, 2002.
Rainen, et al. "Stabilization of Expression Profiles of Genes Associated with the Inflammatory Response in Post-Phlebotomy Whole Blood Using the PAXgeneTM Blood RNA System," *Blood*, vol. 98, Nov. 16, 2001, Abstract only.
Stordeur, et al. "Analysis of Spontaneous mRNA Cytokine Production in Peripheral Blood," *Journal of Immunological Methods*, vol. 261, pp. 195-197, 2002.
Stordeur, et al. "Immune Monitoring in Whole Blood Using Real-Time PCR," *Journal of Immunological Methods*, vol. 276, pp. 69-77, 2003.

* cited by examiner

*Primary Examiner*—Ethan Whisenant
(74) *Attorney, Agent, or Firm*—Knobbe, Martens, Olson & Bear, LLP

(57) ABSTRACT

The present invention is related to a device, kit and method for pulsing a biological sample with a pulsing agent and subsequently stabilizing the biological sample so pulsed. The invention has application in the fields of medical diagnostics, particularly relating to immunity.

51 Claims, 30 Drawing Sheets

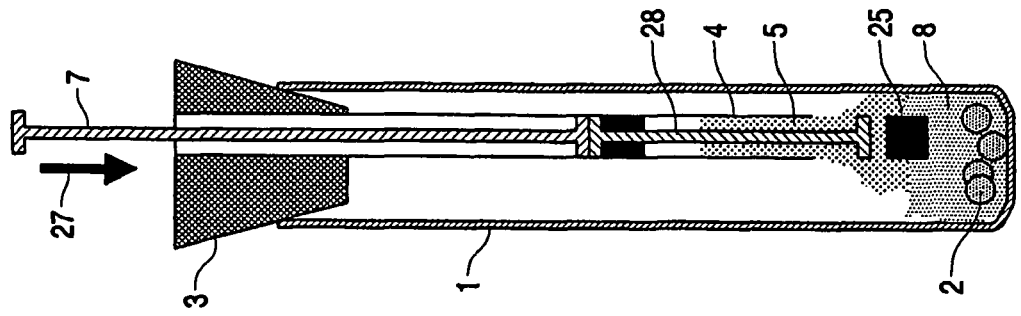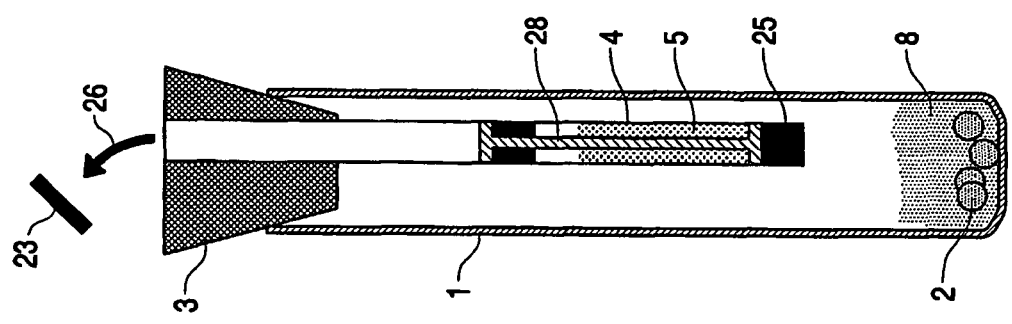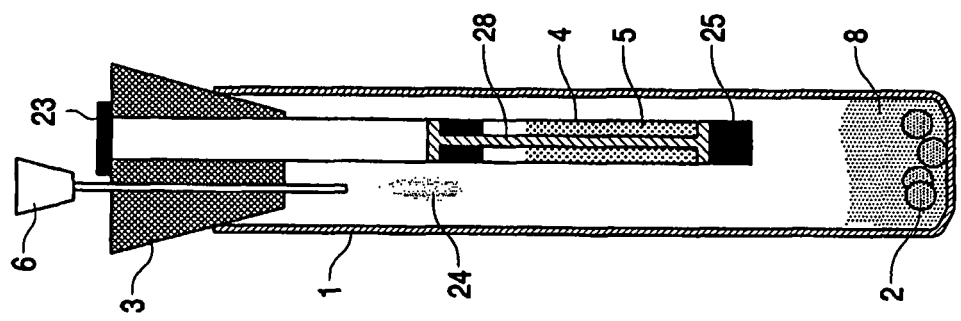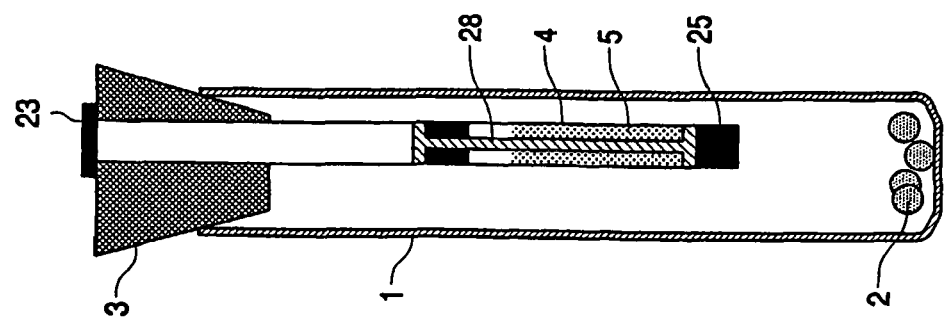

Figure 2:
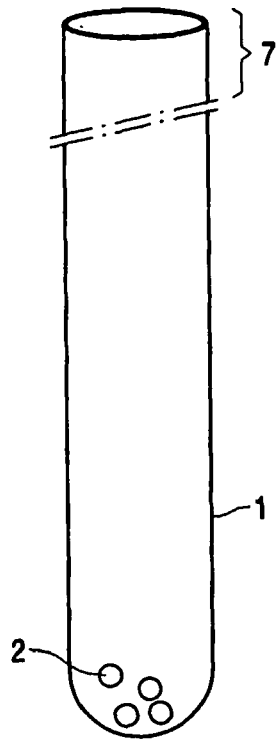

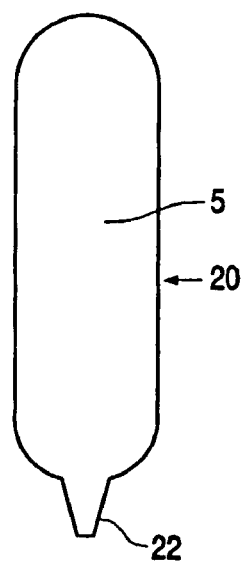
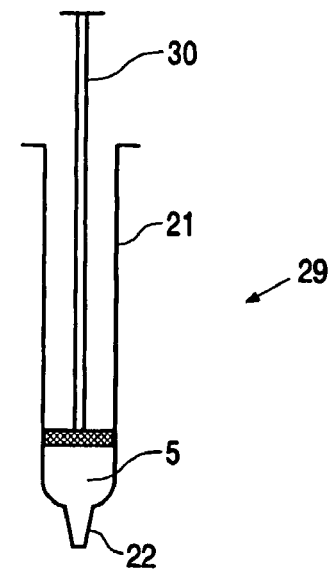
FIG. 9   FIG. 10
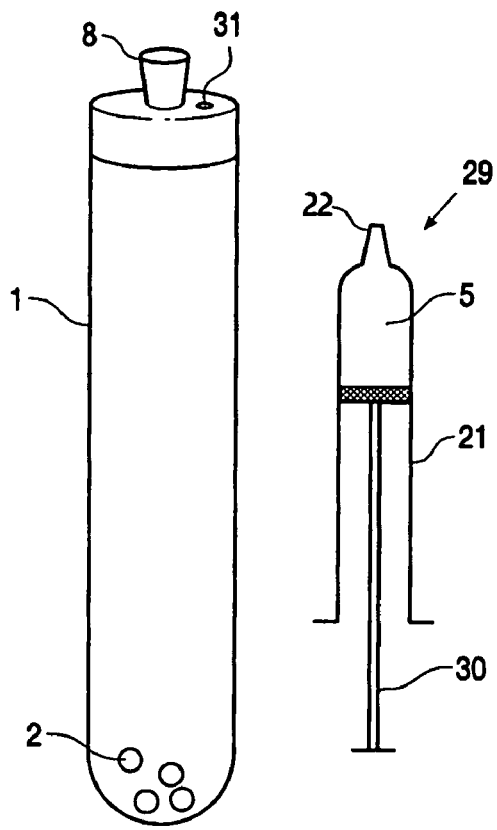
FIG. 11

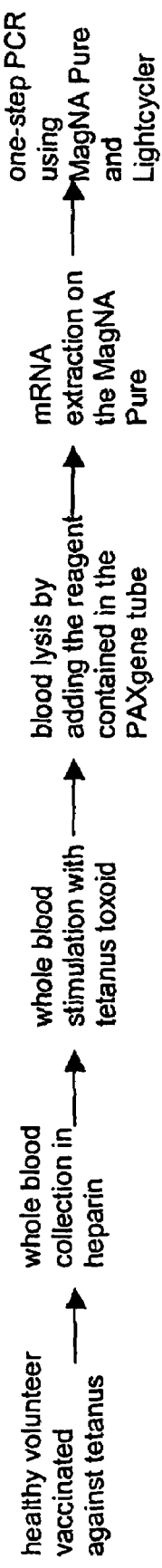
Figure 12. Strategies followed in the given examples
Figure 12.1 *Ex vivo* monitoring of immune response against tetanus toxoid.

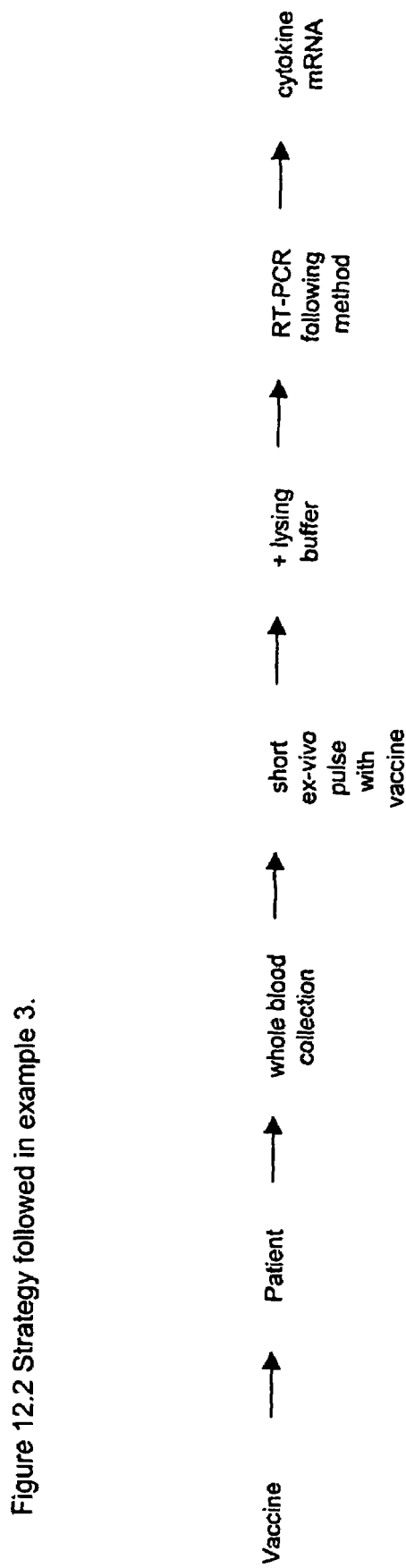
Figure 12.2 Strategy followed in example 3.

Figure 12.3 Strategy followed in example 4
Donor → Recipient organ → whole blood collection → + lysing buffer → RT-PCR following method → cytokine mRNA

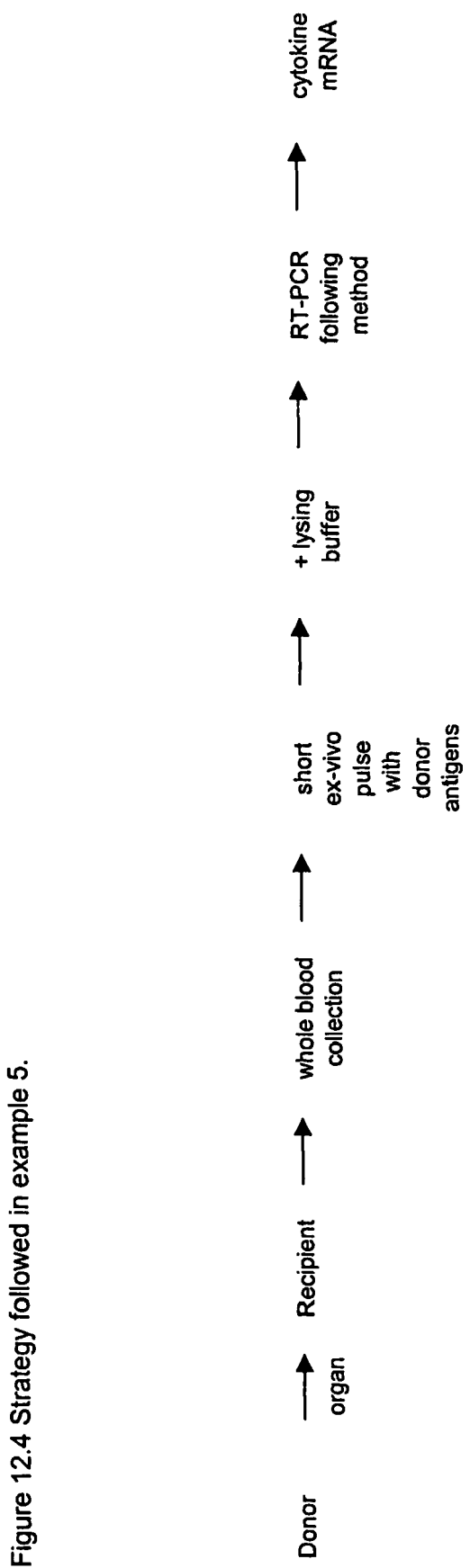
Figure 12.4 Strategy followed in example 5.

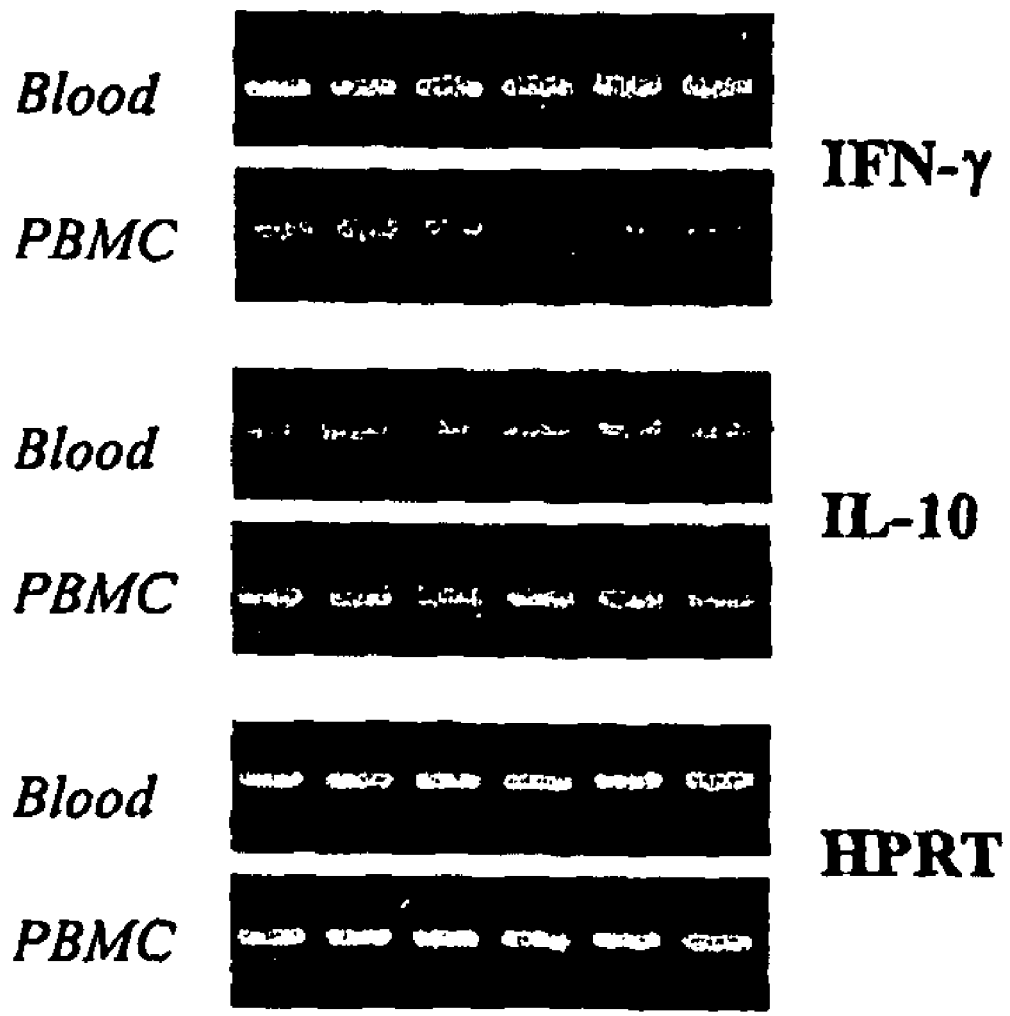
Figure 13.1

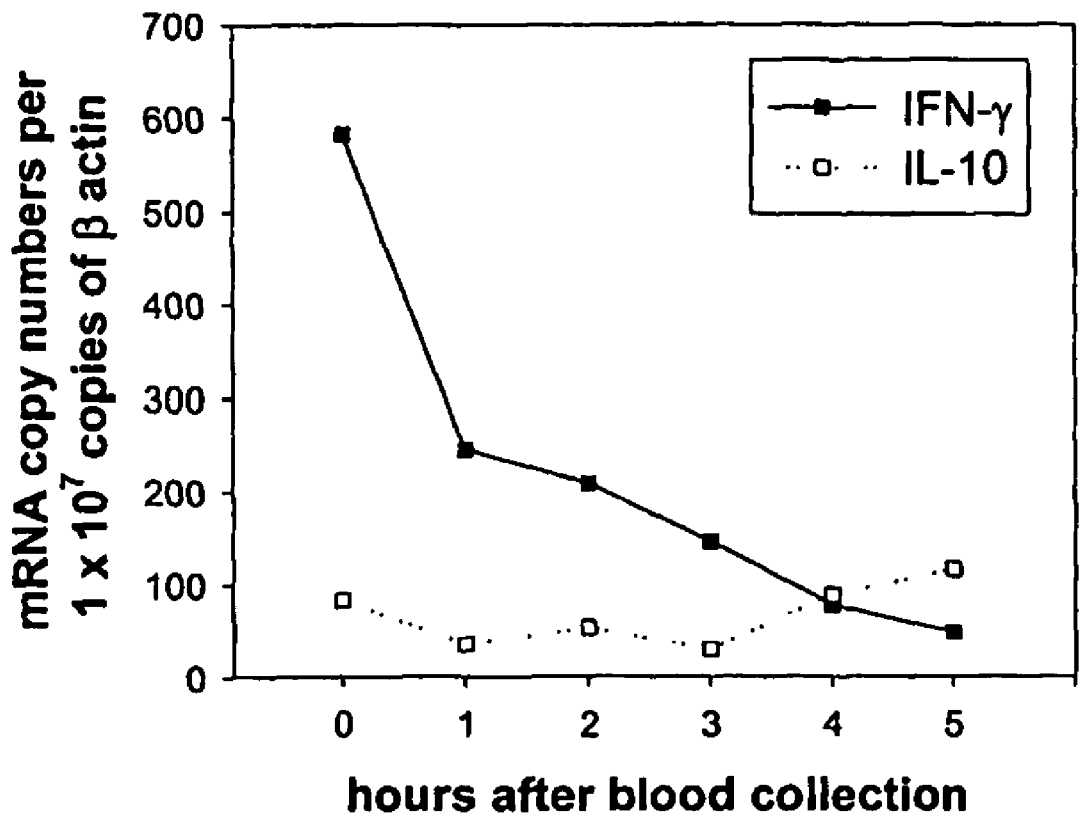
Figure 13.2

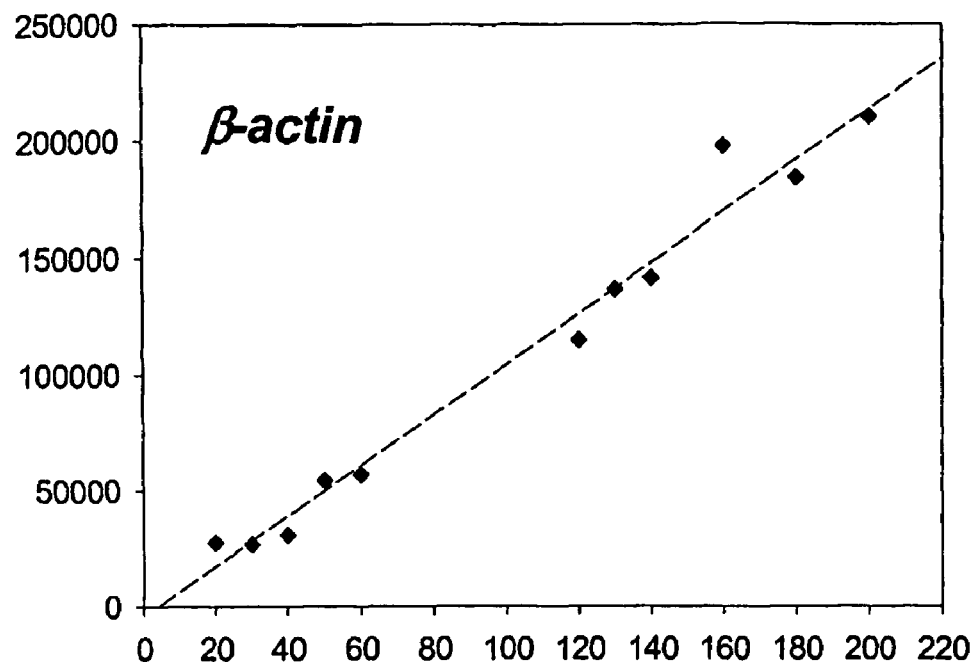
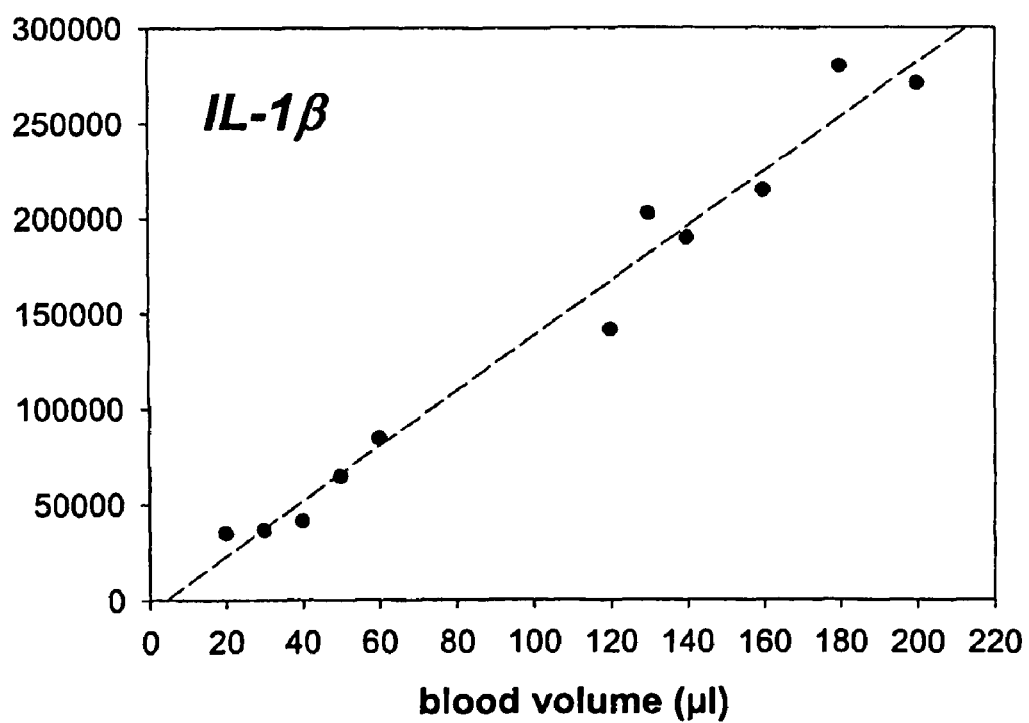
Figure 17

Procedure to analyse blood cytokine mRNA expression

- Whole blood sample incubation in the presence the tested potential immuno-modulator (antigen, allergen, cell, xenobiotic,...)

- Blood cells lysis and mRNA stabilisation using the reagent contained in the *PAXgene* tube

- Automated mRNA extraction and preparation of the reaction mixture for one-step RT-PCR using an automated device (*Magna Pure instrument – Roche Diagnostics*)

- Quantification of cytokine mRNA levels by real-time PCR using the *Lightcycler instrument* (*Roche Diagnostics*)

Figure 21

Automated mRNA extraction and reagent mix preparation on the MagNA Pure : direct correlation between starting cell number and found copy number

Immune monitoring in cancer immunotherapy

- 7/99: melanoma of the right scapula. Excision
- 8/01: SC M+ arm, back, abdomen, right testis
- 4/02: right orchidectomy
- 4/02: pre-vaccine check-up
- 5/02: initiation of the vaccine program

Figure 24

*In vitro* stimulation of whole blood : dose-response to Feld1

IL-4 mRNA levels after whole blood stimulation with Feld1 are higher in allergic patients compared to healthy controls Monitoring of alloreactive immune response : quantification of IL-2 mRNA in a whole blood + dendritic cells system

SEQUENCE LISTING

<160> NUMBER OF SEQ ID NOS: 10

<210> SEQ ID NO 1
<211> LENGTH: 22
<212> TYPE: DNA
<213> ORGANISM: Homo sapiens

<400> SEQUENCE: 1
ctcaccagga tgctcacatt ta                                              22

<210> SEQ ID NO 2
<211> LENGTH: 24
<212> TYPE: DNA
<213> ORGANISM: Homo sapiens

<400> SEQUENCE: 2
tccagaggtt tgagttcttc ttct                                            24

<210> SEQ ID NO 3
<211> LENGTH: 23
<212> TYPE: DNA
<213> ORGANISM: Homo sapiens
<220> FEATURE:
<221> NAME/KEY: misc_feature
<222> LOCATION: (1)...(1)
<223> OTHER INFORMATION: 6Fam label
<220> FEATURE:
<221> NAME/KEY: misc_feature
<222> LOCATION: (23)...(23)
<223> OTHER INFORMATION: Tamra-p label

<400> SEQUENCE: 3
tgcccaagaa ggccacagaa ctg                                             23

-continued

```
<210> SEQ ID NO 4
<211> LENGTH: 21
<212> TYPE: DNA
<213> ORGANISM: Homo sapiens

<400> SEQUENCE: 4
actttgaaca gcctcacaga g                                              21

<210> SEQ ID NO 5
<211> LENGTH: 20
<212> TYPE: DNA
<213> ORGANISM: Homo sapiens

<400> SEQUENCE: 5
ttggaggcag caaagatgtc                                                20

<210> SEQ ID NO 6
<211> LENGTH: 21
<212> TYPE: DNA
<213> ORGANISM: Homo sapiens
<220> FEATURE:
<221> NAME/KEY: misc_feature
<222> LOCATION: (1)...(1)
<223> OTHER INFORMATION: 6Fam label
<220> FEATURE:
<221> NAME/KEY: misc_feature
<222> LOCATION: (21)...(21)
<223> OTHER INFORMATION: Tamra-p label

<400> SEQUENCE: 6
ctgtgcaccg agttgaccgt a                                              21

<210> SEQ ID NO 7
<211> LENGTH: 22
<212> TYPE: DNA
<213> ORGANISM: Homo sapiens

<400> SEQUENCE: 7
tgtcacaaac agtgcaccta ct                                             22

<210> SEQ ID NO 8
<211> LENGTH: 26
<212> TYPE: DNA
<213> ORGANISM: Homo sapiens

<400> SEQUENCE: 8
agttacaata ggtagcaaac cataca                                         26

<210> SEQ ID NO 9
<211> LENGTH: 21
<212> TYPE: DNA
<213> ORGANISM: Homo sapiens

<400> SEQUENCE: 9
taattgcctc acattgtcac t                                              21

<210> SEQ ID NO 10
<211> LENGTH: 21
<212> TYPE: DNA
<213> ORGANISM: Homo sapiens

<400> SEQUENCE: 10
attcagctcg aacactttga a                                              21
```

DEVICE, KIT AND METHOD FOR PULSING BIOLOGICAL SAMPLES WITH AN AGENT AND STABILISING THE SAMPLE SO PULSED

RELATED APPLICATIONS

This is the U.S. National Phase under 35 U.S.C. §371 of International Application PCT/EP2003/007453, filed Jul. 10, 2003.

FIELD OF THE INVENTION

The present invention relates to devices, method and kits for use in diagnostic assays, and has applications in the field of immunology.

INTRODUCTION

Monitoring nucleic acid levels, for example, those of mRNA is valuable in ascertaining directly the effect of an agent on a biological system. For example, if an agent is introduced into a biological system for a defined length of time, the reaction of the system to the agent can be determined by measuring the levels of mRNA. This may be useful in monitoring immunity wherein, for example, the agent is an antigen and the mRNA monitored is cytokine mRNA e.g. interleukins.

Testing the impact of an agent by withdrawing blood from an individual and adding the agent at a later point in time introduces a variable delay between the blood being out of circulation and stimulation with the agent. During the delay, the blood may undergo slow or fast chemical modification, depending, for example, on the temperature at which it is held. Furthermore, a delay which is variable means comparative studies between consecutively withdrawn samples are invalid.

When testing for nucleic acid, a major challenge is due to the instability of RNA in vitro especially when there is a requirement for the detection of low-level RNA or unstable RNA. Even the degradation of only a small fraction of the RNA may change the interpretation of the levels of RNA. Some transcripts are known to be present at low copy in a cell; other transcripts have an "AU-rich" sequence in their 3' end promoting their fast degradation by endogenous RNAses. Studies have shown that RNA rapidly degrades significantly within hours after sample collection. Furthermore, certain species of RNA, through the process of gene induction, increase once the sample is collected. Both RNA degradation and in vitro gene induction can lead to an under- or over-estimation of the in vivo gene transcript number.

When measuring the effect of an agent on withdrawn blood, therefore, a challenge in the art is to manage the process of mRNA degradation which begins immediately after the blood is withdrawn and resumes after the introduction of antigen. Because the 'before' degradation can have an impact on the 'after' degradation, the error is coupled to two processes; hence the potential for error is greater and the error is more difficult to delineate.

Another problem in the art is the necessity for several pieces of equipment in performing an exposure of a biological sample to an agent followed by a subsequent nucleic acid analysis thereof. Typically, reagent bottles, accurate pipettors, refrigeration means are at least required to perform quantitative measurements. If samples are being taken in the absence of suitable laboratory facilities, for example in the home of an individual or in a basically-equipped surgery, it may not be suitable or convenient to perform accurate substrate additions, and furthermore refrigeration facilities might not be available.

Once a sample has been exposed to an agent, many methods exist to isolate and measure nucleic acids therein, for example mRNA. Some methods allow even the determination of low-level transcripts out of a pool of transcripts. However, none of them provide the possibility to determine the level(s) of transcript(s) present in the biological sample at the time of the sampling. Even under refrigerated conditions, the storage of biological samples leads to incorrect mRNA levels. Indeed, in practice, the analysis of fresh sample is not feasible as the place of sampling and the place of RNA analysis are located differently.

Recently, PreAnalytiX (a joint venture between Becton Dickinson and Qiagen) produced the PAXgene™ Blood RNA System. The PAXgene™ Blood RNA System (also referred to as the Qiagen method) is an integrated and standardized system for the collection and stabilization of whole blood specimens and isolation of cellular RNA. According to PreAnalytix in the PAXgene™ Blood RNA System, blood is collected directly into PAXgene™ Blood RNA Tubes and RNA is subsequently isolated using the PAXgene™ Blood RNA Kit. Using this system, intact cellular RNA can be retrieved from whole blood.

The PAXgene™ Blood RNA Tube is a plastic, evacuated tube, for the collection of whole blood and stabilization of the cellular RNA profile. The tubes contain an additive (a proprietary blend of reagents) that stabilizes cellular RNA and may eliminate ex vivo induction of gene transcription and prevents the drastic changes in the cellular RNA expression profiles that normally take place in vitro. RNA is then isolated using silica-gel-membrane technology supplied in the PAXgene™ Blood RNA Kit. According to PreAnalytiX the resulting RNA accurately represents the expression profile in vivo and is suitable for use in a range of downstream applications. According to the supplier, accurate quantification of gene transcripts is possible using this system. A major disadvantage of this PAXgene™ Blood RNA System is that respective PAXgene™ Blood RNA Tube needs to be combined with the PAXgene™ Blood RNA Kit (see instruction manual of the PAXgene™ Blood RNA Tubes). This obliged combination, however, limits further improvement of the system.

AIMS OF THE INVENTION

One aim of the present invention is to provide a device, kit and method for exposing a biological sample to an agent and stabilising the nucleic acid in the sample so exposed.

Another aim of the present invention is to provide a device, kit and method which reduces, makes constant, or makes nearly constant the time between obtaining the biological sample and exposing said sample to an agent.

Another aim of the present invention is to provide a device, kit and method which reduces, makes constant or makes nearly constant the time from which the sample is exposed to an agent and the nucleic acid in said sample is stabilised.

Another aim of the present invention is to provide a device, kit and method which exposes an agent to a sample without the need to measure an amount of sample and/or agent.

Another aim of the present invention is to provide a device, kit and method which exposes an agent to a sample without the need to measure an amount of stabilising agent Another aim of the present invention is provide a device, kit and method for exposing a biological sample to an agent, stabilising the nucleic acid in the sample so exposed and extracting the nucleic acid therefrom for further analysis.

Another aim of the present invention is provide a device, kit and method which addresses a combination of one or more of the aforementioned aims.

SUMMARY OF THE INVENTION

One embodiment of the present invention is a vessel suitable for accepting a liquid biological sample, exposing said sample to a first substance and subsequently a nucleic acid stabilising agent, said vessel comprising:
a) a first substance present inside said vessel,
b) a container in which said stabilising agent is present,
c) a connection between the inside of said vessel and the inside of said container,
d) a physical barrier that temporarily blocks said connection.

Another embodiment of the present invention is a vessel as described above wherein said first substance is immobilised on part or all of the inside surface of said vessel.

Another embodiment of the present invention is a vessel as described above wherein said first substance is immobilised on a solid support.

Another embodiment of the present invention is a vessel as described above wherein said first substance is a liquid.

Another embodiment of the present invention is a vessel as described above wherein said first substance is a solid.

Another embodiment of the present invention is a vessel as described above comprising one or more areas suitable for puncture by a syringe needle.

Another embodiment of the present invention is a vessel as described above wherein said area is a re-sealable septum.

Another embodiment of the present invention is a vessel as described above comprising a fitting suitable for receiving a syringe and transmitting the contents therein to the interior of said vessel.

Another embodiment of the present invention is a vessel as described above comprising a fitting suitable for receiving a syringe needle.

Another embodiment of the present invention is a vessel as described above comprising a cannular suitable for withdrawing bodily fluids.

Another embodiment of the present invention is a vessel as described above comprising a valve which is capable of minimising the flow of gas/liquid from vessel, and allowing the flow of liquid biological sample into the vessel.

Another embodiment of the present invention is a vessel as described above comprising a means through which displaced gas may be expelled.

Another embodiment of the present invention is a vessel as described above wherein said vessel is held under negative pressure.

Another embodiment of the present invention is a vessel as described above wherein the physical barrier of item d) is opened by the application of physical force to said vessel.

Another embodiment of the present invention is a vessel as described above wherein said force transmits an opening means to said physical barrier.

Another embodiment of the present invention is a vessel as described above wherein said force irreversibly opens said physical barrier.

Another embodiment of the present invention is a vessel as described above wherein said vessel comprises an indication for dispensing a known volume of stabilising agent therein.

Another embodiment of the present invention is a vessel as described above wherein said first substance comprises one or more immune system antigens.

Another embodiment of the present invention is a vessel as described above wherein said immune system antigens are vaccine components.

Another embodiment of the present invention is a vessel as described above wherein said immune system antigens are antigens which provoke a hyperallergenic response.

Another embodiment of the present invention is a vessel as described above wherein said immune system antigens are one or more selected from histocompatibility antigens, bacterial LPS, tetanous toxoid, a cancer immunotherapy antigen, MAGE-3, a cat allergen, Feld1, antigen presenting cells from an organ donor, an autoantigen, GAD65.

Another embodiment of the present invention is a vessel as described above wherein said stabilising agent is an inhibitor of cellular RNA degradation and/or gene induction.

Another embodiment of the present invention is a vessel as described above wherein said inhibitor of cellular RNA degradation and/or gene induction is that as found in a PAXgene™ Blood RNA Tube.

Another embodiment of the present invention is a method of pulsing a sample of blood with an antigen, subsequently inhibiting cellular RNA degradation and/or gene induction therein and subsequently testing RNA components in the stabilised blood sample so pulsed comprising the use of a vessel as described above.

Another embodiment of the present invention is a method of testing the immune response of an individual towards an antigen comprising the use of a vessel as described above wherein the first substance is the antigen under investigation, comprising the steps of.
a) introducing a sample of blood taken from said individual into the vessel,
b) optionally agitating said vessel,
c) introducing after a pre-determined period of time, said nucleic add stabilising agent into said vessel, and
d) testing the levels of mRNA.

Another embodiment of the present invention is a method as described above where step
d) further comprises the steps of
e) forming a precipitate comprising nucleic acids,
f) separating said precipitate of step (e) from the supernatant,
g) dissolving said precipitate of step (f using a buffer, forming a suspension,
h) isolating nucleic acids from said suspension of step (g) using an automated device,
i) dispersing/distributing a reagent mix for RT-PCR using an automated device,
j) dispersing/distributing the nucleic acids isolated in step (h) within the dispersed reagent mix of step (i) using an automated device, and,
k) determining the in vivo levels of transcripts using the nucleic acid/RT-PCR reagent mix of step (j) in an automated setup.

Another embodiment of the present invention is a method as described above wherein the immune response of an individual towards an antigen against which the individual has been pre-immunised is tested, the first substance is the antigen under investigation and the levels of cytokine mRNA are tested.

Another embodiment of the present invention is a method as described above wherein said cytokine is one or more of IL-2, IL-4, IL-13, IFN-gamma.

Another embodiment of the present invention is a method as described above wherein the hyperallergenicity of an individual towards an antigen is tested, the first substance is the antigen under investigation and the levels of IL-4 mRNA are tested.

Another embodiment of the present invention is a method as described above wherein the rejection of an organ transplant in an individual towards an antigen is tested, wherein the first substance is a histocompatibility antigen of the donor and the levels of IL-2 mRNA are tested.

Another embodiment of the present invention is a use of a vessel as described above for pulsing a sample of blood with an antigen, subsequently inhibiting cellular RNA degradation and/or gene induction therein and subsequently testing RNA components in the stabilised blood sample so pulsed.

Another embodiment of the present invention is a use of a vessel as described above for extracting a pre-determined volume sample of blood from an individual using said needle or cannular, pulsing said sample with an antigen, subsequently inhibiting cellular RNA degradation and/or gene induction therein and subsequently testing RNA components in the stabilised blood sample so pulsed.

Another embodiment of the present invention is a kit suitable for pulsing a liquid biological sample with a first substance, and subsequently introducing an agent that inhibits cellular RNA degradation and/or gene induction thereto, and testing mRNA components in the stabilised blood sample so pulsed, said kit comprising:
a) a vessel in which said first substance is present, and
b) a container in which said agent is present Another embodiment of the present invention is a kit as described above wherein the inside of said vessel and the inside of said container are connected, and a physical barrier temporarily blocks said connection.

Another embodiment of the present invention is a kit as described above wherein said first substance is immobilised on part or all of the inside surface of said vessel.

Another embodiment of the present invention is a kit as described above wherein said first substance is immobilised on a solid support.

Another embodiment of the present invention is a kit as described above wherein said first substance is a liquid.

Another embodiment of the present invention is a kit as described above wherein said first substance is a solid.

Another embodiment of the present invention is a kit as described above wherein said vessel comprises one or more openings.

Another embodiment of the present invention is a kit as described above said vessel comprises one or more areas suitable for puncture by a syringe needle.

Another embodiment of the present invention is a kit as described above wherein said area is a re-sealable septum.

Another embodiment of the present invention is a kit as described above wherein said vessel comprises one or more fittings suitable for receiving a syringe and transmitting the contents therein to the interior of said vessel.

Another embodiment of the present invention is a kit as described above wherein said vessel comprises one or more fittings suitable for receiving a hypodermic syringe needle.

Another embodiment of the present invention is a kit as described above wherein said vessel comprises one or more cannulars suitable for withdrawing bodily fluids.

Another embodiment of the present invention is a kit as described above wherein said vessel comprises one or more valves which are capable of minimising the flow of liquid from vessel, minimising the flow of gas into or from vessel, and/or allowing the flow of liquid biological sample into the vessel.

Another embodiment of the present invention is a kit as described above wherein said vessel comprises one or more means through which displaced gas may be expelled.

Another embodiment of the present invention is a kit as described above wherein said vessel is held under negative pressure.

Another embodiment of the present invention is a kit as described above wherein the physical barrier of item d) is opened by the application of physical force to said vessel.

Another embodiment of the present invention is a kit as described above wherein said force transmits an opening means to said physical barrier.

Another embodiment of the present invention is a kit as described above wherein said force irreversibly opens said physical barrier.

Another embodiment of the present invention is a kit as described above wherein said vessel and/or container comprises an indication for dispensing a known volume of stabilising agent therein.

Another embodiment of the present invention is a kit as described above wherein said first substance comprises one or more immune system antigens.

Another embodiment of the present invention is a kit as described above wherein said immune system antigens are vaccine components.

Another embodiment of the present invention is a kit as described above wherein said immune system antigens are antigens which provokes a hyperallergenic response.

Another embodiment of the present invention is a kit as described above wherein said immune system antigens are are selected from one or more of histocompatibility antigens, bacterial LPS, tetanous toxoid, a cancer immunotherapy antigen, MAGE-3, a cat allergen, Feld1, antigen presenting cells from an organ donor, an autoantigen, and GAD65.

Another embodiment of the present invention is a kit as described above wherein said inhibitor of cellular RNA degradation and/or gene induction is that as found in a PAXgene™ Blood RNA Tube.

Another embodiment of the present invention is a kit as described above for testing the immune response of an individual towards an antigen against which the individual has been pre-immunised wherein the first substance is the antigen under investigation and the mRNA tested is cytokine mRNA.

Another embodiment of the present invention is a kit as described above wherein said cytokine is one or more of IL-2, IL-4, IL-13, IFN-gamma. Another embodiment of the present invention is a kit as described above for testing an individual for hyperallergenicity towards an antigen wherein the first substance is the antigen under investigation and the mRNA tested is IL-4 mRNA.

Another embodiment of the present invention is a kit as described above for testing an individual for rejection of an organ transplant wherein the first substance is a histocompatibility antigen of the donor and mRNA tested is IL-2 mRNA.

Another embodiment of the present invention is a kit as described above further comprising one or more oligonucleotides suitable for said testing said mRNA(s).

DETAILED DESCRIPTION OF THE INVENTION

One aspect of the present invention is related to a vessel suitable for holding a biological sample, said vessel holding a predetermined amount of pulsing agent.

As used herein "pulsing agent" comprises any substance to which a biological sample may be exposed. Examples of substances include peptides, nucleic acids, antigens. The pulsing agent may comprise other components besides the substance, such as stabilising agents, indicators, linkers, matrices, etc.

The term "biological sample" means a sample containing nucleic acids/biological agents such as clinical (e.g. cell fractions, whole blood, plasma, serum, urine, tissue, cells, etc.), agricultural, environmental (e.g. soil, mud, minerals, water, air), food (any food material), forensic or other possible samples. With 'whole blood' is meant blood such as it is collected by venous sampling, i.e. containing white and red cells, platelets, plasma and eventually infectious agents; the infectious agents may be viral, bacterial or parasitical. The clinical samples may be from human or animal origin. The sample analysed can be both solid or liquid in nature. It is evident when solid materials are used, these are first dissolved in a suitable solution, which could be the RNAlater reagent sold by Qiagen. According to the invention, this solution is not always a real "buffer" with at least two well balanced components. It may be a strong hypotonic solution such as NaCl alone or an extraction solution such as with alcohol.

The vessel may hold the pulsing agent in several ways. According to one aspect of the invention, the pulsing agent may be immobilised on the inside wall of the vessel. The inside wall of the vessel may be lined with a suitable coating enabling the pulsing agent to be attached. Alternatively, the pulsing agent may be attached directly to part or all of the inside wall of the vessel. Suitable coatings, methods and vessel materials for suitable for such attachments are known in the art. According to another aspect of the invention the pulsing agent is present as a solid. The solid may be a powder, a freeze-dried pellet, a gel, a cream. Suitable solid compositions and method of their preparation are known in the art. According to another aspect of the invention the pulsing agent is immobilised on a solid support. The solid support may be attached to the inside of the vessel. Alternatively the solid support may be free of the inside of the vessel. Examples of solid supports include, but are not limited to, chromatography matrix, magnetic beads. According to another aspect of the present invention, pulsing agent is present as a liquid. Suitable liquid compositions and method of their preparation are known in the art.

Performing an analytical pulsing experiment outside of laboratory conditions requires calibrated measuring equipment such as pipettors. Errors due to uncalibrated measuring devices can lead to inherent errors and also human error in dispensing can lead to error between different samples, making comparative analysis invalid. Providing a vessel supplied with a pre-determined about of pulsing agent obviates the need for additional equipment and eliminates human measuring errors.

Types of vessel according to the invention can be any suitable for storage of biological samples. According to one aspect of the invention, the vessel containing the pulsing agent is sealed. According to one aspect of the invention, the vessel containing the pulsing agent has a resealing means such as a screw-cap, push-on cap, a flip-cap. See, for example, FIG. 5. According to one aspect of the invention, the biological sample may be introduced into the vessel by puncture, using a syringe needle into the wall of the vessel. The wall of the vessel may be resealable after puncture, or the wall of the vessel may not be resealable after puncture, or the wall of the vessel may be provided with a resealable area such as a septum. See, for example, FIG. 4

According to one aspect of the invention, the biological sample may be introduced into the vessel by means of one or more fittings attached to vessel for receiving a syringe or other container fitted with a coupling means. For example, the vessel might be fitted with a Luer fitting that can receive a needleless syringe. See for example, FIG. 3. In another example, the vessel might be fitted with a non-Luer fitting which can mate with a container having a reciprocating non-Luer design of coupling.

According to one aspect of the invention, the biological sample may be introduced into the vessel by means of a cannular or hypodermic needle fitted to said vessel, suitable for directly withdrawing biological samples from an individual. See, for example, FIG. 6.

According to one aspect of the invention, the biological sample may be introduced into the vessel by opening the resealing means. See, for example, FIG. 5.

As known by the skilled person, the introduction of a sample into a sealed vessel will result in the displacement of an equal volume of air or gas therefrom, or a build up of pressure therein. Therefore, the vessel may be provided with a suitable means to allow displaced gas to exit from said vessel, or to accommodate the build up of pressure. Said means are known the art and include valves, non-drip holes, vents, clothed-vents, expandable vessel walls, use of negative pressure within said vessel. See, for example, arrow 31 on FIG. 11.

In one aspect of the invention the pressure inside the sealed vessel is negative. The negative pressure may be utilised to relieve the pressure build-up upon introduction of biological sample into said sealed vessel. Alternatively, or in addition, the negative pressure may be at a predetermined level and may be utilised so as to allow the introduction of a fixed volume of biological sample.

The vessel in which a pre-determined quantity of pulsing agent is already supplied allows diagnostic tests to be performed on individuals without the necessity for apparatus for measuring out said antigen. Furthermore, when diagnostic test are performed outside laboratory conditions, problems with contamination and dispensing accuracy can lead to false results in a quantitative assay. A vessel as described herein overcomes these problems.

Another aspect of the present invention is related to a vessel as described herein, further comprising a container in which a stabilising agent is present; the stabilising agent is temporarily prevented from coming into contact with the pulsing agent or the biological sample exposed to said agent.

In one aspect of the present invention, the stabilising agent comprises a nucleic acid stabilising agent and/or cellular RNA degradation inhibiting agent and/or a gene induction inhibiting agent, and/or the stabilising agent is as that found in a PAXgene™ Blood RNA Tube. Agents and combinations thereof are known in the art, or can be deduced by the skilled artisan.

The PAXgene™ Blood RNA Tubes are supplied with a solution containing an additive that stabilises cellular RNA and may eliminate ex vivo induction of the gene transcription. No detailed information is provided describing the nature of this additive. The brochure provided with said tubes refers to patent U.S. Pat. No. 5,906,744 for this purpose. Nevertheless, the tube described in this patent allows a person skilled in the art to prepare nucleic acids from plasma and not from whole blood as performed in the present invention. In particular, the device of U.S. Pat. No. 5,906,744 preferably comprises a plastic or glass tube, a means for inhibiting blood coagulation and a means for separating plasma from whole blood (U.S. Pat No. 5,906,744 column 2, 1.42-43). Therefore, according to the present invention, the content as described in U.S. Pat. No. 5,906,744 does not relate to the real content of the PAXgene™ Blood RNA Tube as it relates to a different use.

According to the present invention the solution held in the PAXgene™ Blood RNA Tubes may contain a quaternary amine surfactant. Therefore, according to the present invention, a quaternary amine surfactant may be used as a stabilising agent. The use of a quaternary amine surfactant in order to stabilise nucleic acids in a biological sample has been previously described in U.S. Pat. No. 5,010,183. This patent provides a method for purifying DNA or RNA from a mixture of biological materials. Said method comprises the step of adding a cationic detergent to a mixture containing the RNA or DNA in an amount sufficient to dissolve cells, solubilize any contaminating proteins and lipids in the mixture, and form insoluble hydrophobic complex between the nucleic acid and the detergent. The complex which comprises the RNA or DNA with the detergent thus becomes separated from the solubilised contaminants. In a more recent patent, the same inventors stated that the use of the surfactant, as described in U.S. Pat. No. 5,010,183, and other commercially available surfactants results in inefficient precipitation of RNA and incomplete lysis of blood cells. As there was a need for improved cationic surfactants for this purpose, the inventors of U.S. Pat. No. 5,010,183 searched for a novel method for isolating RNA from a biological sample, including blood, involving the use of an aqueous, cationic surfactant solution comprising a selected quaternary amine (U.S. Pat. No. 5,985,572). New aqueous quaternary amine surfactants, able to stabilize RNA from biological samples, are also described in WO94/18156 and WO02/00599. The synthesis of the different possible surfactants, that can be used in any methods of the present invention, can be performed according to the instructions as published in above cited or related patents. One example of a quaternary amine which can be used in the method of the present invention is tetradecyltrimethyl-ammonium oxalate. (U.S. Pat No. 5,985,572). Alternatively, said cationic detergent may be Catrimox-14TM (U.S. Pat. No. 5,010,183) as shown in the example 1 of the present invention. Further to the stabilization of said biological sample, said applications describe the isolation of the nucleic acids using conventional separation techniques such as column chromatography. Due to the obliged combination of the PAXgene™ Blood RNA Tube with the PAXgene™ Blood RNA kit (which also applies column chromatography) the supplier gives the impression that the compounds present in the PAXgene™ Blood RNA Tube may only be compatible with said chromatographic method.

In one aspect of the present invention, the stabilising agent is contained in said container until such as time as the biological sample has mixed with the pulsing agent and/or a user requires introduction of the stabilising agent.

According to one aspect of the invention, the inside of said container and the inside of said vessel are connected, and a physical barrier that blocks the connection is present. At an appropriate time, an application of force opens the physical barrier, allowing the stabilising agent to mix with the biological sample so-pulsed. According to one aspect of the invention a physical barrier reversibly opens and closes in accordance with the physical force applied. The force applied may transmit to the physical barrier itself, or via the stabilising agent to the physical barrier. Examples of such physical barriers include rotary valve, aperture valve, slit valve, diaphragm valve, ball valve, flap valve. According to another aspect of the invention, the physical barrier may be irreversibly opened by the application of force. The force applied may transmit to the physical barrier itself (see for example, FIG. 7), or via the stabilising agent to the physical barrier (see for example, FIG. 8). Another example of such physical barriers include a plug which is forced out of position (See, for example, FIG. 1), a barrier which shatters upon the application of force (see, for example, FIG. 7).

According to another aspect of the invention, the inside of said container and the inside of said vessel are connected, and the flow of stabilising agent from the container to the vessel is prevented by the surface tension of the stabilising agent in combination with the aperture size of the connection. According to this aspect of the invention, at an appropriate time an application of force which transmits to the stabilising agent, forces the stabilising agent from the container into the vessel. The force may be applied, for example, by squeezing, continually inverting, and agitating.

The vessel as described herein, which comprises a container for dispensing a stabilising agent, allows an untrained technician to pulse blood samples and stabilise the blood so pulsed for analysis by a skilled artisan at a later stage. Thus, where many samples are required to be collected, a vessel as disclosed herein allows a cost saving since unskilled operators can be employed to pulse and stabilise the blood. Furthermore, the vessel allows reproducibility because known amounts of pulsing agent and stabilising agent may be pre-supplied in said vessel, so minimising errors associated with pipetting. Furthermore, the time between withdrawing a biological sample and exposing said sample to a pulsing antigen is greatly reduced since the sample can be drawn directly into said tube, or via a syringe for example. Furthermore, the time between pulsing the biological sample and stabilising the biological sample can be accurately set, since the introduction of stabilising agent to the sample is achieved simply by the application of force; hence there are no delays due to pipetting stabilising agent.

Another embodiment of the present invention is a kit suitable for pulsing a biological sample with a pulsing agent, and subsequently introducing a stabilising agent thereto and testing the RNA components in the biological sample so pulsed, comprising one or more vessel as disclosed above and one or more containers in which said stabilising agent is present.

In one embodiment of the kit, the container in which said stabilising agent is present is not connected to the vessel in which the pulsing agent in present. The container can thus be separate and may be any container of the art, suitable for holding a stabilising agent in a kit. The container may have a resealing means such as a screw-cap, push-on cap, a flip-cap for example. The container may have a breakable seal such as a peel-back adhesive seal, a snap-off seal. The container might comprise one or more fittings suitable for attachment of said vessel fitted reciprocal coupling means and transfer of stabilising agent to said vessel. For example, the container might be fitted with a Luer fitting that can receive reciprocal Luer fitting attached to said vessel as described above (see, for example, FIGS. 9, 10 and 11). In another example, the container might be fitted with a non-Luer fitting which can mate with a vessel having a reciprocating non-Luer design of coupling. The stabilising agent might be transferred to the vessel by opening the resealing means of the vessel; the stabilising agent may exit the container via any of the aforementioned fittings or openings. The container may optionally have a means to allow air to enter while stabilising agent exits. In one aspect of the invention, the container may have a means to force stabilising agent from said container; examples include but are not limited to a syringe-type plunger, squeezable walls of the container. The container optionally has a measuring means to determine the volume of stabilising agent being dispensed, for example, a scale. In one aspect of the invention, the container holds a volume of stabilising agent sufficient for single use. In another aspect of the invention, the container holds a volume of stabilising agent sufficient for multiple pulsing experiments.

In another embodiment of the kit, the container in which said stabilising agent is present is connected to the vessel in which the pulsing agent in present: embodiments of the vessel are described above.

Optionally, a kit of the present invention may comprise an instruction manual comprising a description of a method for pulsing a biological sample.

Another aspect of the present invention is related to a vessel and a kit comprising said vessel as disclosed herein wherein said pulsing agent comprises an antigen. According to one aspect of the invention said antigen is bacterial LPS. According to another aspect of the invention said antigen is an immune response recall antigen. According to another aspect of the invention said antigen is tetanus toxoid. According to another aspect of the invention said antigen is a cancer immunotherapy antigen. According to another aspect of the invention said antigen is MAGE-3. According to another aspect of the invention said antigen is a cat allergen. According to another aspect of the invention said antigen is Feld1. According to another aspect of the invention said antigen is antigen presenting cells from an organ donor. According to another aspect of the invention said antigen is an autoantigen. According to another aspect of the invention said antigen is GAD65.

Another aspect of the present invention is related to a method of pulsing a biological sample with an antigen, and subsequently stabilising the nucleic acid therein and testing the RNA components in the stabilising biological sample so pulsed. The method comprises the use of a vessel and/or kit as disclosed herein to optionally collect, pulse and stabilise the sample.

In one embodiment of the present invention, a method of pulsing a biological sample comprises the steps of:
i) introducing a biological sample into said vessel,
ii) optionally agitating said vessel,
iii) introducing stabilising agent into said vessel after a pre-determined period of time, and
iv) testing the levels of nucleic acid therein.

Another embodiment of the present invention is method of testing the immune response of an individual towards an antigen against which the individual has been pre-immunised comprising the use of a vessel as disclosed herein wherein the pulsing agent is the antigen under investigation and the steps of.
a) introducing a sample of blood taken from said individual into the vessel,
b) optionally agitating said vessel,
c) after a pre-determined period of time, introducing said nucleic acid stabilising agent into said vessel
d) testing the levels of cytokine mRNA.

According to one aspect of the invention the cytokine is one or more of IL-2, IL-4, IL-13, IFN-gamma.

Another embodiment of the present invention is method of testing an individual for hyperallergenicity towards an antigen comprising the use of a vessel as disclosed herein wherein the pulsing agent is the antigen under investigation and the steps of:
e) introducing a sample of blood taken from said individual into the vessel,
f) optionally agitating said vessel,
g) after a pre-determined period of time, introducing a nucleic acid stabilising agent into said vessel
h) testing the levels of IL-4 mRNA.

Another embodiment of the present invention is method of testing an individual for rejection of an organ transplant comprising the use of a vessel as disclosed herein wherein the pulsing agent is a histocompatibility antigen of the donor and the steps of:
i) introducing a sample of blood taken from said individual into the vessel,
j) optionally agitating said vessel,
k) after a pre-determined period of time, introducing a nucleic acid stabilising agent into said vessel
l) testing the levels of IL-2 mRNA.

Another aspect of the invention relates to a method of pulsing a biological sample with an antigen, and subsequently stabilising the nucleic acid therein and testing the RNA components in the stabilising biological sample so pulsed, comprising the steps of.
A) Pulsing said biological sample with a pulsing agent and adding a compound inhibiting RNA degradation and/or gene induction thereto, using a kit, device and/or method as disclosed above,
B) forming a precipitate comprising nucleic acids,
C) separating said precipitate of step (B) from the supernatant,
D) dissolving said precipitate of step (C) using a buffer, forming a suspension,
E) isolating nucleic acids from said suspension of step (D) using an automated device,
F) dispensing/distributing a reagent mix for RT-PCR using an automated device,
G) dispensing/distributing the nucleic acids isolated in step (E) within the dispensed reagent mix of step (F) using an automated device, and,
H) determining the in vivo levels of transcripts using the nucleic acid/RT-PCR reagent mix of step (G) in an automated setup.

Inhibition of RNA degradation and/or gene induction at the moment of the biological sampling is crucial in order to retrieve a pool of RNAs which can be used to determine the in vivo transcript levels. Cellular RNA can be purified using the PAXgene™ Blood RNA System in its complete form, however, the present invention proves that real in vivo levels can not be measured using this system 'as such' (see example 2).

The present invention shows that the in vivo levels of nucleic acid transcripts can only be measured/determined/quantified when starting from a pool of RNA prepared from a stabilised biological sample, using a compound inhibiting extra- and/or intracellular RNA degradation and/or gene induction; whereby the isolation of the nucleic acids is performed using an automated device, whereby the reagent mix and the isolated nucleic acids, used for the RT-PCR reaction, are dispensed using an automated device, and whereby the determination of the transcript levels is performed in an automated setup. According to the present invention, only this approach allows the quantification of in vivo RNA in a reproducible manner. The number of steps performed in said method is reduced to a minimum in order to avoid errors. An 'error' may be a pipetting-, a handling-, a procedural- and/or a calculation error or any error which can be made by a person skilled in the art. In this respect the present invention suggests to perform the RT and the PCR reaction in one step. The method of the present invention will even be more accurate when combining more intermediate steps. For example, in the method of the present invention steps (A) and (B) can be combined.

In another aspect of the present invention, the dispension of the nucleic acids (step (G)) may be performed after, before or simultaneously with the dispension of the reagent mix needed for RT-PCR (step (F)).

According to the method of present invention, OD measurements do not need to be performed, eliminating the errors made in the calculation of the nucleic acid concentration. In contrast, using the complete PAXgene™ Blood RNA kit OD measurements need to be made. This illustrates again that the method according to present invention is a more reliable and accurate method compared to the latter system. This better accuracy of the present invention is illustrated by the reproducibility studies presented in Table 1.

In another aspect of the present invention, when dissolving the formed precipitate in step (D) of the method according to the present invention, the obtained suspension can be used in combination with an RNA extraction method and an analyzing method which are fully automated. It is only this combination which allows the accurate optimisation and reproducibility of the performed method and which allows the accurate and reproducible determination of RNA levels after pulsing. As the brochure of the PAXgene™ Blood RNA System describes that the corresponding tubes can not be used in combination with other isolation methods, and no detailed information is available describing the different compositions of the kit, it is not obvious for a person skilled in the art to use parts of this PAXgene™ Blood RNA System and develop a new method therefrom.

There exist only few commercial systems which allow the isolation of RNA fully automatically. Examples of such automated nucleic acid extractors are: the MagNA Pure LC Instrument (Roche Diagnostics), The AutoGenprep 960 (Autogen), the ABI PrismTM 6700 Automated Nucleic Acid Workstation (Applied Biosystems), WAVE® Nucleic Acid Analysis System with the optional WAVE® Fragment Collector FCW 200 (Transgenomic) and the BioRobot 8000 (Qiagen).

The present invention points towards the fact that for all these systems it is essential to start with material which is as fresh as possible or which is stabilised in order to allow the determination transcript level after pulsing, wherein RNA degradation is minimised. The problem for all these systems is that the biological sample is collected and brought to the laboratory in tubes that contain no or only a conventional additive, so that mRNA can still be rapidly degraded. Consequently, mRNA quantification using these methods will undoubtedly lead to the quantification of the transcripts present in the tube, but this quantification does not represent the transcript levels present in the cells/biological agent at the moment of sampling. Experimental evidence of this is provided in FIG. 13.2 of example 1 of the present invention.

The term 'quantification' is meant accurate and reproducible determination of RNA copy numbers; but it is trivial for a person skilled in the art that also qualitative or semi-quantitative studies can be performed using RNA isolated via a method as described by the present invention.

The definition 'transcript' is not limited to messenger RNA (mRNA) but also relates to other types of RNA molecules known to exist by a person skilled in the art. According to the method of the present invention mRNA as well as total RNA can be extracted. This allows to get a correct estimation of the in vivo nuclear RNA, providing a powerful tool to evaluate gene transcription.

The term 'nucleic acid' refers to a single stranded or double stranded nucleic acid sequence, said nucleic acid may consist of deoxyribonucleotides (DNA) or ribonucleotides (RNA), RNA/DNA hybrids or may be amplified cDNA or amplified genomic DNA, or a combination thereof. A nucleic acid sequence according to the invention may also comprise any modified nucleotide known in the art.

According to the present invention, the nucleic acid may be present extra- or intracellularly in the biological sample.

The 'separation' of the precipitate from the supernatant in step (C) of present method can be performed via centrifugation, filtration, absorption or other means known by a person skilled in the art. Said precipitate may include cells, cell/debris, nucleic acids or a combination thereof. The basis of the concept is to stop the nucleic-acid-containing-agent (or biological agent) from having contact with external sources/pulses/signals. This can be performed by fixing, lysing and/or disintegrating the nucleic-acid-containing-agent, or by any other means known by a person skilled in the art.

The buffer used in step (D) of the method of present invention may be a buffer to dissolve the precipitate obtained in step (C) of said method. This buffer may have additional effects such as lysis or further lysis of the nucleic-acid-containing-agent.

The 'automated device' used may be an automated pipetting device or another automated device known by a person skilled in the art suitable for carrying out the indicated actions.

With a 'reagent mix for RT-PCR' is meant all reagents needed for a simultaneous RT and PCR reaction (with the exception of the oligonucleotides when explicitly mentioned). According to the present invention, 'oligonucleotides' may comprise short stretches of nucleic acids as found in for example primers or probes. According to the present invention, this method can be used in combination with micro-arrays or RNase protection assays.

As pointed out before, storage of biological samples such as blood leads to incorrect determination of mRNA levels. Indeed, in practice, the analysis of fresh sample is not feasible as the place of sampling and the place of RNA analysis is located differently. The method according to the present invention allows the transport biological samples from a remote site to a suitable laboratory without any effect on their in vivo transcript content. Transport of the biological sample can be performed after step (A) or step (B) in the method of the present invention.

Usually, when using blood samples, red blood cells are preferentially eliminated before the nucleic acids are isolated. Red blood cells are rich in haemoglobin and their presence results in the production of highly viscous lysates. Therefore, removal of these allows to isolate nucleic acids in a more improved fashion. However, in the method of the present invention, this step is eliminated as an insoluble precipitate is immediately formed comprising the nucleic acids, separating these from all other components of the biological sample. This illustrates that, in addition to other advantages, the method of the present invention is a superior method in comparison with most prior art methods.

According to the present invention, said buffer used in step (D) of a method of the present invention may be a guanidine-thiocyanate-containing buffer.

In the examples of the present invention the precipitate formed in the PAXgene™ Blood RNA Tubes is dissolved in the lysis buffer as provided by the MagNA Pure LC mRNA Isolation Kit I (Roche Diagnostics, Molecular Biochemicals). Therefore, it is suggested in the present invention that one of the possible buffers which may be used in the method of the present invention is a guanidine-thiocyanate-containing lysis buffer as provided by MagNA Pure LC mRNA Isolation Kit I (Roche Diagnostics, Molecular Biochemicals).

The MagNA Pure LC mRNA Isolation Kit I (Roche Diagnostics, Molecular Biochemicals) is especially designed for use on the MagNA Pure LC Instrument, to guarantee the isolation of high quality and undegraded RNA from whole blood, white blood cells, and peripheral blood lymphocytes. According to its product description, obtained RNA is suitable for highly sensitive and quantitative LightCycler RT-PCR reactions, as well as for standard block cycler RT-PCR reactions, Northern blotting and other standard RNA applications. Nevertheless, the present invention proves that the use of this method 'as such' could not result in the determination of correct transcript levels. The present invention shows that there is a need to stabilize the RNA prior to the RNA isolation (see example 1). The present invention describes the unique combination of the use of RNA stabilizing compounds and an automated isolation/analysis procedure.

According to the present invention, once the precipitate of step (D) is dissolved in a lysis buffer such as the one provided by MagNA Pure LC mRNA Isolation Kit I, the method of the present invention may follow the procedure as described for the MagNA Pure LC mRNA Isolation Kit I. After the samples are lysed through the presence of a chaotropic salt in the lysis buffer, streptavidin-coated magnetic particles are added together with biotin-labeled oligo-dT, and the mRNA binds to the surface of the particles. This is followed by a DNase digestion step. mRNA is then separated from unbound substances using a magnet and several washing steps. Finally, the purified mRNAs are eluted. This isolation kit allows the automated isolation of pure mRNA as a "walk away" system. It allows to isolate mRNA of high quality and integrity suitable for all major downstream applications regarding gene expression analysis. Different protocols are offered depending on the sample material used. The samples may be set directly on the MagNA pure LC Instrument stage. When using whole blood, cells present in the samples are preferentially lysed manually. mRNA isolation may then be postponed or directly further processed on the instrument.

The present invention proves in the present examples that the use of the MagNA Pure LC Instrument (Roche Diagnostics, Molecular Biochemicals) as automated device in step (E), step (F) and/or step (G) of the method according to the present invention leads to the production of a pool of RNA which can be used to determine exact levels of transcripts after exposure to a pulsing agent. RNA-capturing beads such as magnetic beads, coated with oligo-dT via a streptavidin-biotin system or an equivalent system, may be applied in the method of the present invention in order to separate mRNA from the cellular debris.

Alternatively, according to the present invention other automated devices may be used such as the ABI Prism™ 6700 Automated Nucleic Acid Workstation (Applied Biosystems) or any other automated device that can be used for this purpose.

In the brochure of the MagNA pure LC mRNA Isolation Kit I (Cat No 3 004 015) no compositions of the buffers used in this kit are mentioned in detail. Therefore it is not obvious for a person skilled in the art to assume that the buffer as provided by this kit would allow to dissolve the pellet obtained by the method of the PAXgene™ Blood RNA Tubes. In addition, a person skilled in the art would not combine both methods based on the information provided by the PAXgene™ Blood RNA Tubes brochure stating that these tubes can only be combined with the corresponding PAXgene™ Blood RNA Kit (page 3, see limitations of the system; page 6, see ordering information).

As pointed out above, when using blood samples, red blood cells are preferentially lysed after step (A) in the method of the present invention. In the design of the MagNA Pure LC mRNA Isolation Kit I (Roche Diagnostics, Molecular Biochemicals) there is a possibility to lyse and eliminate red blood cells, before mRNA isolation from white blood cells. Nevertheless, because of this step, samples cannot be treated fast enough to avoid mRNA degradation. The present inventors decided to use the stabilising agent contained in the PAXgene™ Blood RNA Tube in conjunction with the MagNA Pure mRNA Isolation Kit on the MagNA Pure Instrument. Using the PAXgene™ Blood RNA Tubes provides a precipitate of nucleic acids that is not supposed to be soluble in the lysis buffer of the MagNA Pure mRNA Isolation Kit. Despite of this, the inventors found that it is actually possible. Following this observation, the inventors combined the use of the stabilising agent in the PAXgene™ Blood RNA Tubes with the use of an automated RNA isolation system. The inventors found surprisingly that this combination is possible and that this combination provides a powerful technique for the accurate mRNA quantification from biological samples.

The RNA isolated using the method according to the present invention is ready for use in a wide range of downstream applications, including for instance nucleic acid amplification technologies, such as RT-PCR and NASBA®, Expression-array and expression-chip analysis, Quantitative RT-PCR, including TaqMan® technology, cDNA synthesis, RNase and S1 nuclease protection, Northern, dot, and slot blot analysis and primer extension.

The present inventors showed in the example 1 and example 2 of the present invention that the use of a compound inhibiting RNA degradation and/or gene induction in conjunction with an automated RNA isolation and an automated analysis method such as real time PCR allows the determination of in vivo levels of transcripts. Nevertheless, according to present invention analysis methods other than real-time PCR may be applied as long as they are provided in an automated setup.

A main advantage of the method according to the present invention, is the fact that by using this method small sample volumes can be analyzed. This is of prime importance when only small volumes are available, for example when analyzing neonatal blood samples or in cases of high blood loss. According to the present invention RNA quantification may be performed using a biological sample as small as 100 µl. The analysis of RNA from a sample as small as 100 µl is not possible with the Qiagen kit (PAXgen™ Blood RNA System) which requires a larger volume of blood (2.5 ml following the kit handbook).

As mentioned above, one aspect of the present invention is a kit suitable for pulsing a biological sample with a pulsing agent, and subsequently stabilising the nucleic acid from the biological sample so pulsed. In another aspect of the invention, the said kit comprises additional components for isolating quantifiable RNA from the stabilised, pulsed biological samples. According to an aspect of the invention, the kit may comprise additional components such as:
  reagents for automated RNA isolation,
  a reagent mix for a simultaneous RT and real-time PCR reaction or separate compounds thereof, allowing the automated dispension of said mix,
  optionally, specific oligonucleotides to perform said RT-PCT reactions, and,
  optionally, an instruction manual describing a method for an automated RNA isolation, a method for the automated dispension of a reagent mix and the dispension of the isolated nucleic acids for RT- real time PCR, and a method for automated RNA analysis.

In the present examples the present inventors apply the "Lightcycler mRNA hybridisation probes kit" from Roche Diagnostics, Molecular Biochemicals (cat # 3 018 954) to perform the RT-PCR reactions in one step. All reagents needed are included in this kit, except the oligonucleotides (synthesized by Biosource). Nevertheless, real time PCR as described in the present invention can also be performed on other instruments such as the Applied Biosystems instruments. The kit may additionally comprise a buffer such as a guanidine-thiocyanate-containing buffer which can be used in step (b) of the method according to the present invention.

The method according to the present invention can also be used for the quantification/detection of DNA (double or single stranded) in biological samples. Therefore, the present invention also relates to a method for the quantification of DNA from a biological sample wherein a method is used as performed for the quantification of RNA according to the present invention, wherein the RT reaction is skipped and wherein the compound of step (a) also protects the DNA from being degraded. As these nucleic acids are more stable than RNA, its stabilization is less important than for RNA.

In addition, the present invention relates to a kit for isolating quantifiable DNA from a biological sample according to the present invention, wherein a reagent mix/compounds for performing said RT reaction is absent Situations where exact DNA levels need to be determined in biological samples may be to determine the 'presence' of infection(s)/contamination(s) in biological samples by unexpected genes, pathogens or parasites; and/or to determine the 'level' of said infection/contamination. For example the method may be used to determine the percentage of transgenic material in a cereal batch.

The present invention also relates to the use a device, kit and method, according to the present invention, for the monitoring/detection of changes of in vivo nucleic acids of a biological marker in a biological sample after pulsing with an agent, in order to diagnose a certain disease.

The present invention also relates to the use a device, kit and method according present invention, for the monitoring/detection of changes of in vivo nucleic acids of a biological marker in a biological sample after pulsing with an agent, in order to screen for a compound, said compound used for the production of a medicament for curing a disease. Therefore, the invention also relates to a compound identifiable by a method according to present invention.

The devices, kits, and methods disclosed herein may be used to treat and/or diagnose diseases. An example of the disease to be cured or diagnosed is an immuno-related disease. According to the invention, examples of immuno-related diseases may be autoimmunity, rheumatoid arthritis, multiple sclerosis, Type 1 diabetes mellitus, cancer (e.g. in cancer immunotherapy), immunodeficiencies (e.g. in AIDS), allergy, graft rejection or Graft versus Host Disease (GVHD) (e.g. in transplantation). The examples enclosed in the present application illustrate said applications in detail. Therefore, a immunomodulatory compound or agent may influence one of said diseases; the change of the immuno-related transcripts or the epitope specific CTLs-related or T Helper lymphocyte-related transcripts may indicate the presence and/or the status of one of said diseases; as well as the immunological status which may illustrate the status of one of said diseases.

Nucleic acids which may be quantified using the devices, kits, and methods of the present invention in order to study said immuno-related disease may be nucleic acids coding for, for example, chemokines, cytokines, growth factors, cytotoxic markers, transcription factors, members of the TNF-related cytokine-receptor superfamily and their ligands, apoptosis markers, immunoglobulins, T-cell receptor, and any marker related to the activation or the inhibition of the immune system known or to be discovered.

According to the invention, said nucleic acids may code for a marker such as IL-1ra, IL-1β, IL-2, IL-4, IL-5, IL-9, IL-10, IL-12p35, IL-12p40, IL-13, TNF-α, IFN-γ, IFN-α, TGF-β, and any interleukin or cytokine involved or not in the immune response. House keeping genes such β-actin or GAPDH (glyceraldehyde phosphate deshydrogenase) could be used as internal marker.

According to the invention said epitope specific CTLs-related or T Helper lymphocyte-related transcripts be a nucleic acid coding for cytokines, cytokine receptors, cytotoxines, inflammatory or anti-inflammatory mediators, members of the TNF-related cytokine-receptor superfamily and their ligands, G-protein coupled receptors and their ligands, tyrosine kinase receptors and their ligands, transcription factors, and proteins involved in intra-cellular signaling pathways.

According to the present invention, said nucleic acid may code for a marker for any of granzyme, perforines, prostaglandins, leukotrienes, immunoglobulin and immunoglobulin superfamily receptors, Fas and Fas-ligand, T cell receptor, chemokine and chemokine receptors, protein-tyrosine kinase C, protein-tyrosine kinase A, Signal Transducer and Activator of Transcription (STAT), NF-kB, T-bet, GATA-3, Oct-2.

The present invention also describes a use of a device, method or a kit according to the present invention, for the detection/monitoring/screening of a compound, wherein said compound is an immunomodulatory compound which may be chosen from the group consisting of eukaryotic cells, prokaryotic cells, viruses, phages, parasites, drugs (natural extracts, organic molecule, peptide, proteins, nucleic acids), medical treatment, vaccine and transplants. The use of such a method is not limited to detect/monitor/screen a single compound. Synergetic effects of group of substances can also be studied.

The present invention also relates to the use of any of the devices, kits, and methods as described above, for the detection/monitoring of epitope specific CTLs or immuno-related transcripts.

The devices, kits, and methods according to the present invention can also be applied for the monitoring of in vivo immunological responses after the treatment of patients with a drug/treatment/vaccine susceptible to modify their immune status. According to the invention, the detection of cytokine mRNA (can be extended to chemokine, growth factors, cytotoxic markers, apoptosis markers, or any marker relate to the activation of the immune system known or to be discovered) with the described method in whole blood of patients under therapy or enrolled in clinical trials with an immunomodulator drug or treatment or with a vaccine (therapeutic or prophylactic) may be used to evaluate the efficiency, the safety and/or the eventual by-side effects of the therapy.

The present invention also relates to a devices, kits, and methods for the detection of in vivo immunological status for the diagnostic/prognostic of diseases affecting the immune system (cancer, auto-immune diseases, allergy, transplant rejection, GVHD, etc.)

According to the invention, the detection of cytokine mRNA (can be extended to chemokine, growth factors, cytotoxic markers, apoptosis markers, or any marker relate to the activation of the immune system known or to be discovered) with the described method in whole blood of patients suffering a disease that affects directly of indirectly their immune system with the aim to dress a diagnosis or prognosis.

The present invention also describes a method to identify an agent capable of modifying the immunological status of a subject via the analysis of epitope specific CTLs comprising the steps of (a) applying an immunomodulatory agent(s) into a subject,
(b) sampling whole blood from said subject, (c) pulsing blood cells present in the whole blood sample of step (b) with an identical similar and/or different immunomodulatory agent as applied in step (a), using a device as described above, (d) collecting pulsed blood cells of step (c) or non-pulsed blood cells of step (b) in a tube comprising a compound inhibiting RNA degradation and/or gene induction, or adding said compound to the pulsed/non-pulsed cells, (e) forming a precipitate comprising nucleic acids, (f) separating said precipitate of step (e) from the supernatant, (g) dissolving said precipitate of step (f) using a buffer, forming a suspension, (h) isolating nucleic acids from said suspension of step (g) using an automated device, (i) dispensing/distributing a reagent mix for RT-PCR using an automated device, (j) dispensing/distributing the nucleic acids isolated in step (h) within the dispensed reagent mix of step (i) using an automated device, (k) detecting/monitoring/analyzing the in vivo levels of epitope specific CTLs-related transcripts in the dispensed solution of step (j) in an automated setup, and, (l) identify agents able to modify the immunological status of said subject, whereby, in case the agent of step (a) is already present in the subject, step (a) is omitted.

The present invention also relates to a kit comprising components enabling execution of at least step (c) above. The kit may contain additional reagents and instructions to enable one or more of the other steps to be executed. The disclosures made herein instruct the skilled artisan of the components required to build the desired kit.

According to the present invention the immunomodulatory agent(s) may be present in case of a disease or in the presence of a transplant in said subject. In the present invention the 'epitope specific CTLs-related transcripts' may be transcripts coding for cytokines, cytokine receptors, cytotoxines (like granzyme, perforines, etc.), members of the TNF-related cytokine-receptor superfamily and their ligands (ex: Fas and Fas-ligand) or other cellular receptors.

The present invention also describes a method to identify an agent capable of modifying the immunological status of a subject:

(a) applying an immunomodulatory agent(s) into a subject, (b) sampling whole blood from said subject, (c) pulsing blood cells present in the whole blood sample of step (b) with an identical/similar and/or different immunomodulatory agent as applied in step (a), using a device or kit as described above, (d) collecting pulsed blood cells of step (c) or non-pulsed blood cells of step (b) in a tube comprising a compound inhibiting RNA degradation and/or gene induction, or adding said compound to the pulsed/nonpulsed cells, (e) forming a precipitate comprising nucleic acids, (f) separating said precipitate of step (e) from the supernatant, (g) dissolving said precipitate of step (f) using a buffer, forming a suspension, (h) isolating nucleic acids from said suspension of step (g) using an automated device, (i) dispensing/distributing a reagent mix for RT-PCR using an automated device, (j) dispensing/distributing the nucleic acids isolated in step (h) within the dispensed reagent mix of step (i) using an automated device, (k) detecting/monitoring/analyzing the in vivo levels of immuno-related transcripts in the dispensed solution of step (j) in an automated setup, and, (l) identify agents able to modify the immunological status of said subject, whereby, in case the agent of step (a) is already present in the subject, step (a) is omitted.

The present invention also relates to a kit comprising components enabling execution of at least step (c) above. The kit may contain additional reagents and instructions to enable one or more of the other steps to be executed. The disclosures made herein instruct the skilled artisan of the components required to build the desired kit.

In the present invention the 'immuno-related transcripts' may be transcripts coding for e.g. cytokine(s), chemokines(s), growth factors, cytotoxic markers, transcription factors, members of the TNF-related cytokine-receptor superfamily and their ligands, or any markers related to activation of the immune system known or to be discovered. According to the present invention the immunomodulatory agent(s) may be present in case of a disease or in the presence of a transplant in said subject. The subject according to the present invention may be of both human or animal origin.

The present invention also provides a method for the diagnosis/prognosis/monitoring of a clinical status affecting the immune system in a subject comprising the steps of:

(a) sampling whole blood from said subject, (b) pulsing blood cells present in the whole blood sample of step (a) with an identical/similar and/or different immunomodulatory agent as present in the subject, using a device or kit as described above, (c) collecting pulsed blood cells of step (b) in a tube comprising a compound inhibiting RNA degradation and/or gene induction, or adding said compound to the pulsed cells, (d) forming a precipitate comprising nucleic acids, (e) separating said precipitate of step (d) from the supernatant, (f) dissolving said precipitate of step (e) using a buffer, forming a suspension, (g) isolating nucleic acids from said suspension of step (f) using an automated device, (h) dispensing/distributing a reagent mix for RT-PCR using an automated device, (i) dispensing/distributing the nucleic acids isolated in step (g) within the dispensed reagent mix of step (h) using an automated device, (j) detecting/monitoring/analyzing the in vivo levels of immuno-related transcripts in the dispensed solution of step (i) in an automated setup, and, (k) detecting/monitoring the change in in vivo levels of immuno-related transcripts, and, (l) diagnosing/prognosing/monitoring the disease affecting the immune system.

In the present invention 'clinical status' is any change of the physical condition of a subject such as different diseases or presence of transplants.

The present invention also relates to a kit comprising components enabling execution of at least step (c) above. The kit may contain additional reagents and instructions to enable one or more of the other steps to be executed. The disclosures made herein instruct the skilled artisan of the components required to build the desired kit.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can be used in the practice or testing of the present invention. All publications and other references mentioned herein are incorporated by reference in their entirety. In case of conflict, the present specification, including definitions, will control. The materials, methods, and examples are illustrative only and not intend to be limiting. Other features and advantages of the invention will be apparent from the following figures, detailed description, and from the claims.

FIGURES

FIGS. 1a to 1d depict an example a vessel and method according to the invention. FIG. 1a shows a vessel 1 wherein antigen particles 2 are present The vessel is fitted with a resealable means of entry 3 for a syringe needle. A container 4 is also part of the vessel 1; stabilising agent 5 being present in the container, and the connection between the inside of the vessel 1 and the inside of the container 4 being temporarily blocked by a physical barrier, in this case, a plug 25. A means of transmitting physical force to dislodge the plug is provided in the form of a plunger 28. In this example, the plunger is covered with a cap 23. In FIG. 1b, biological sample is introduced into the vessel by way of a syringe needle 6, through the resealable means of entry 3, and the biological sample 8, is allowed to be exposed to the antigen 2. In FIG. 1c, the plunger cap 23 is removed 26. In FIG. 1d, a shaft 7 is introduced and pressure applied thereto 27, so forcing the plunger 28 to push the plug 25 away from the container 4. Upon removal of the plug 25, stabilizing agent 5 is released into the vessel 1 and allowed to mix with the biological sample 8 and antigen 2.

Figure 7:
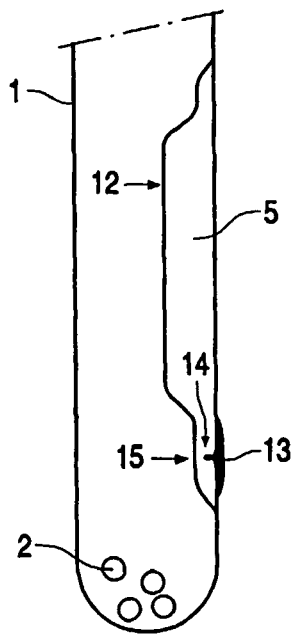
Figure 8:
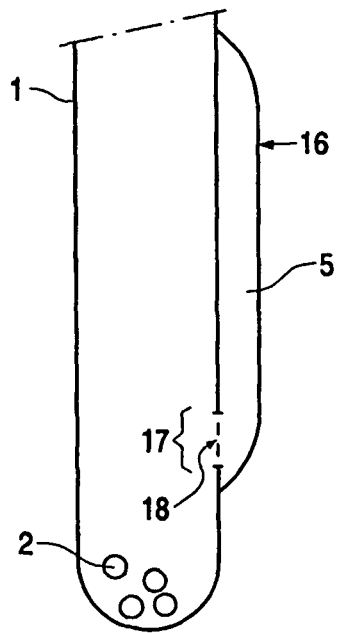

FIG. 2 depicts an example of a vessel 1 according to the invention in which antigen 2 is present. The vessel may be open-topped 7, as shown here, or may be fitted with closures or means to introduce sample or stabilizing agent, examples of which are shown in FIGS. 3 to 6. The body of the vessel 1, may also comprise a container in which stabilising agent is present as shown in FIGS. 7 and 8.

Figure 3:
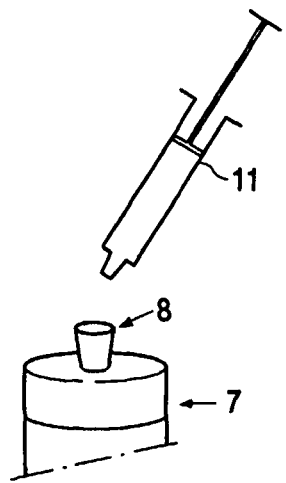

FIG. 3 depicts an example of a fitting suited for a type of vessel shown in FIG. 2. The top of the vessel 7, is fitted with a Luer-type fitting 8 that can receive a reciprocal Luer type fitting on a synringe 11. The syringe may contain biological sample or stabilising agent according to embodiments of the invention.

Figure 4:
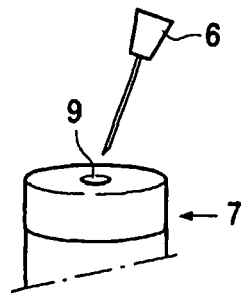

FIG. 4 depicts an example of a fitting suited for a type of vessel shown in FIG. 2. The top of the vessel 7, is fitted with a resealable septum 9 that can receive a syringe needle. The syringe may contain biological sample or stabilising agent according to embodiments of the invention.

Figure 5:
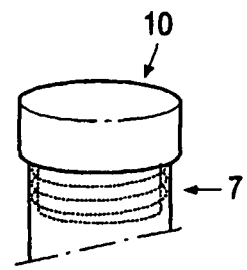

FIG. 5 depicts an example of a fitting suited for a type of vessel shown in FIG. 2. The top of the vessel 7, is fitted a means to receive with a screw cap 10.

Figure 6:
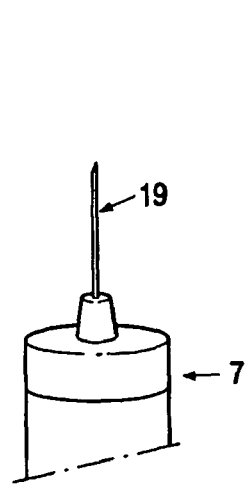

FIG. 6 depicts an example of a fitting suited for a type of vessel shown in FIG. 2. The top of the vessel 7, is fitted a hypodermic syringe needle 19. The vessel might be used directly to withdraw a sample from an individual.

FIG. 7 depicts an example of a body of a vessel 1 which could, for example, be used in combination with the vessels and fittings shown in FIGS. 2 to 6. The vessel 1, in which antigen 2 is present, comprises a container 12 in which stabilizing agent 5 is present. The wall of the container is made entirely or in part 15 from a material which shatters upon the application of a certain force. The container is fitted with a means to transmit force from the user to shatter part or all of the container, comprising a depressable area 13 attached to a sharp point 14. Upon depression of the area 13, the sharp point 14 contacts the shatterable material 15, causing it to shatter, so removing the physical barrier between the container and the vessel, allowing the stabilising agent to flow into the vessel 1 at a time determined by the user.

FIG. 8 depicts an example of a body of a vessel 1 which could, for example, be used in combination with the vessels and fittings shown in FIGS. 2 to 6. The vessel 1, in which antigen 2 is present, comprises a container 16 in which stabilizing agent 5 is present. The connection between the inside of the container and the vessel 17 is physically blocked by a septum 18 which is breachable by the application of force. Upon squeezing the wall of the container 16, pressure is transmitted to the septum, causing the septum to breech so allowing the entry of stabilising agent 5 into the vessel 1.

FIG. 9 depicts an example of a container 20 of the invention which is not connected to a vessel. The stabilising agent 5 is present in the container 20 and the container 20, is fitted with a Luer-type fitting 22 suitable for coupling with a vessel having a reciprocal fitting (for example as shown in FIG. 3 and FIG. 11). The walls of the container 20 may be squeezable, allowing the stabilizing agent to exit upon the application of force thereto.

FIG. 10 depicts an example of a container 29 of the invention which is not connected to a vessel. The stabilising agent 5 is present in the container 29 and the container 29, is fitted with a Luer-type fitting 22 for coupling with a vessel having a reciprocal fitting (for example as shown in FIG. 3 and FIG. 11). The vessel is further fitted with a plunger, the application of force on which allows the stabilizing agent 5 to exit.

FIG. 11 depicts an example of a kit according to the invention, comprising a vessel 1 fitted with a Luer type fitting 8 and, in this instance, a valve 31 allowing the exit of displaced air from vessel. The kit also comprises a container 29, similar to that depicted in FIG. 10, in which stabilizing agent 5 is present. The fitting on the vessel 8 is capable of coupling to the fitting on the container 22.

FIG. 12. Strategies followed in the given examples

FIG. 12.1 Ex vivo monitoring of immune response against tetanus toxoid.

FIG. 12.2 Strategy followed in example 3.

FIG. 12.3 Strategy followed in example 4

FIG. 12.4 Strategy followed in example 5.

FIG. 13.1: RT-PCR for spontaneous production of IFN-γ and IL-10 mRNAs in peripheral blood. Total RNA was extracted from whole blood and from PBMC, as stated, from six different healthy volunteers (columns 1 to 6). Whole blood: 0.6 ml of whole blood were mixed with 6 ml of Catrimox-14™, within the minute that follows sample collection. The samples were then centrifuged at 12000 g for 5 min. The resulting nucleic acids pellet was carefully washed with water, and dissolved in 1 ml of Tripure™. RNA extraction was then carried out according to Tripure™ manufacturer's instructions. PBMC: cells were prepared following standard procedures from 15 ml of heparinized venous blood, and lysed in 1 ml of Tripure™ for RNA extraction. RT-PCR for IFN-γ, IL-10 and housekeeping gene HPRT were performed for all samples from 1 µg total RNA as described (Stordeur et al., (1995), Pradier et al., (1996)).

FIG. 13.2: Real time PCR for IFN-γ and IL-10 mRNA stability in whole blood. A sample of citrated venous blood was collected from healthy donors. From this sample, a 100 µl aliquot was mixed with 900 µl of Catrimox-14™, within the minute that follows blood collection, and every hour after during five hours, the blood sample being simply kept at room temperature between each aliquot taking. The resulting nucleic acids pellet (see legend to FIG. 13.1) was dissolved in 300 µl lysis buffer from the "MagNA Pure LC mRNA Isolation Kit I" (Roche Diagnostics, Molecular Biochemicals). mRNA was extracted using the MagNA Pure LC Instrument (Roche Diagnostics, Molecular Biochemicals) following manufacturer's instructions (final elution volume: 100 µl).

Reverse transcription and real time PCR were performed in one step, following the standard procedure described in the "Lightcycler—RNA Master Hybridisation Probes Kit" (Roche Diagnostics, Molecular Biochemicals), starting from 5 μl of the mRNA preparation. Primers and probes sequences, and PCR conditions, are described in Stordeur et al, J Immunol Methods, 259 (1-2): 55-64, 2002).

Figure 14:
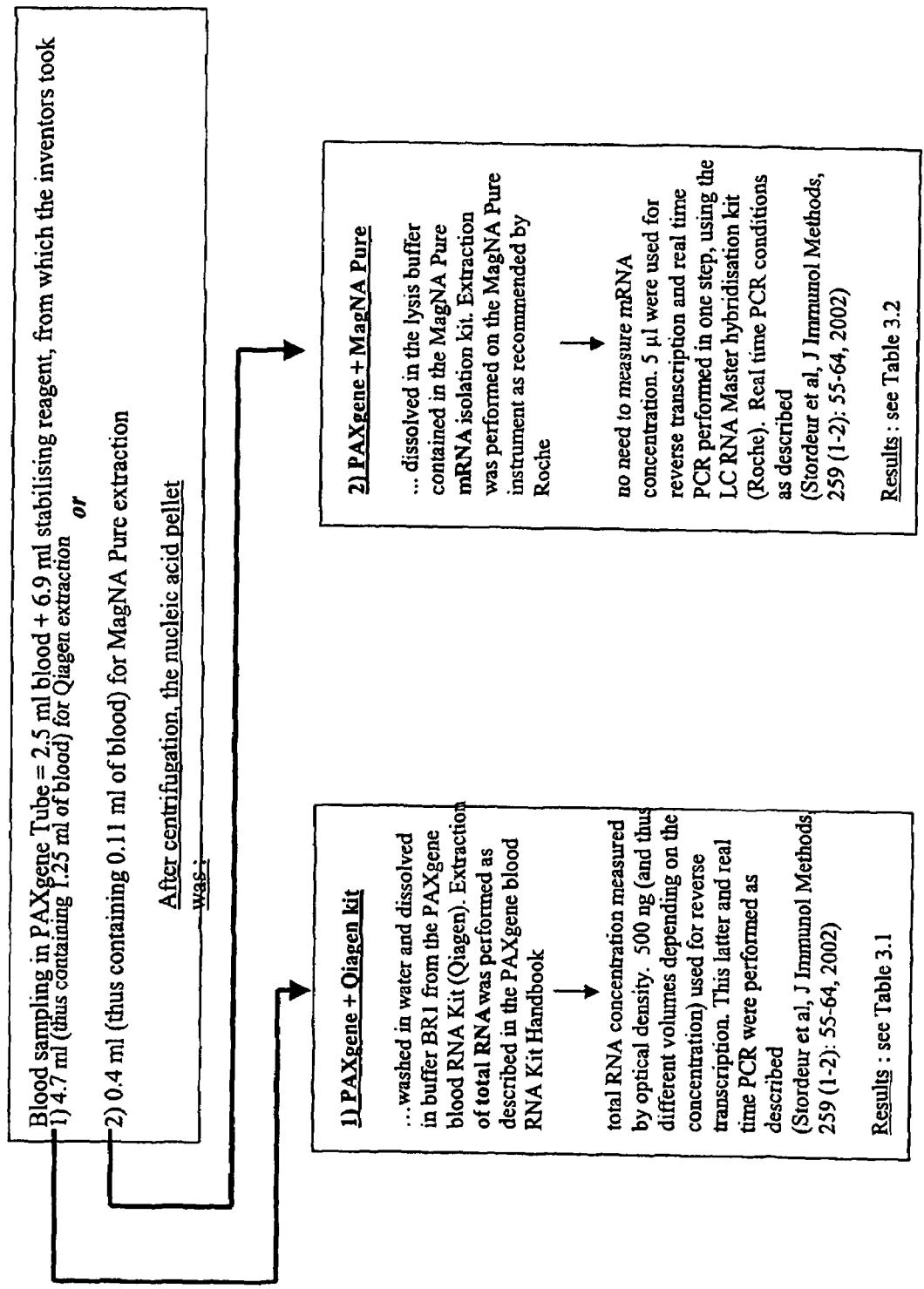

FIG. 14: Schematic comparison of the RNA extraction method from whole blood as suggested by PreAnalytiX compared to method as proposed by the present invention.

Figure 15:
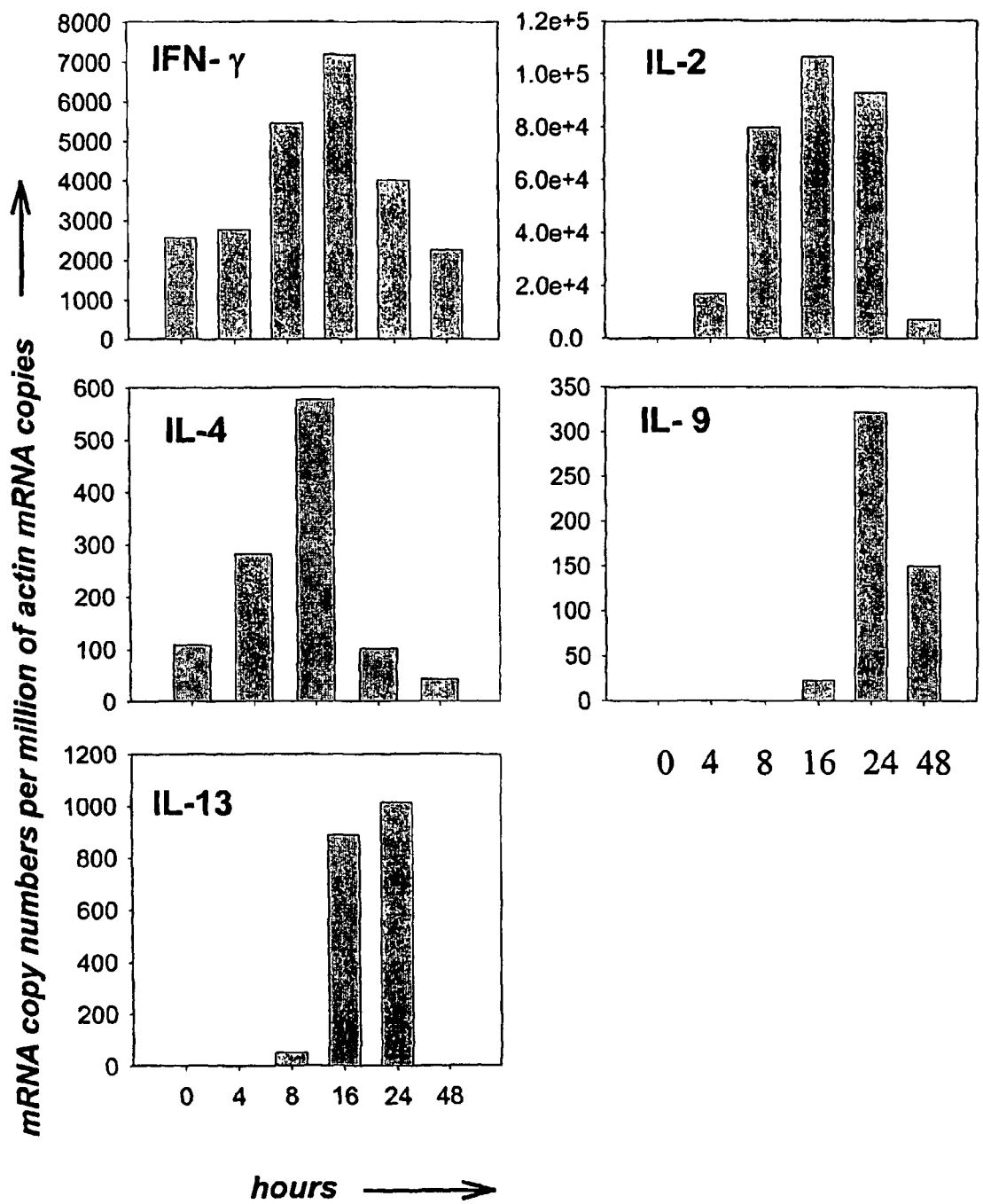

FIG. 15. Cytokine blood mRNA ex vivo induction by tetanus toxoid. Tetanus toxoid (10 μg/ml, Aventis) was added to 500 μl whole blood collected from healthy volunteer vaccinated against tetanus seven years ago. After different time periods at 37° C. in a 5% $CO_2$ atmosphere, 1.4 ml of the reagent contained in the PAXgene tube was added. 300 μl of the obtained lysate were used to isolate total mRNA on the MagNA Pure instrument, and RT-PCR was performed as described in the present invention.

Figure 16:
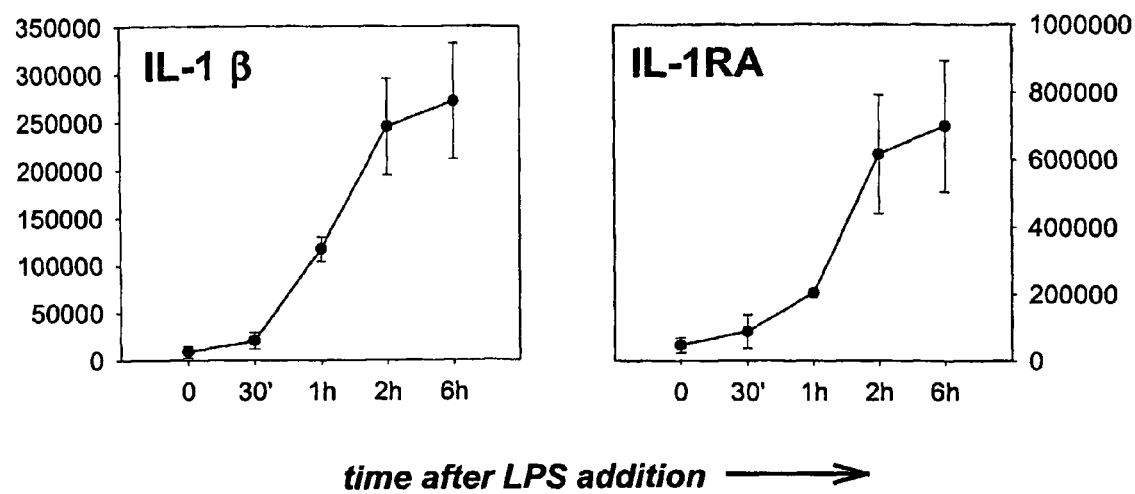

FIG. 16. IL-1β and IL-1 RA mRNA kinetics after whole blood stimulation with LPS. 200 μl of heparinized blood were incubated with 10 ng/ml LPS for 0 (beginning of the culture), 0.5, 1, 2 and 6 hours. At the end of the culture, 500 μl of the PAXgene™ tube's reagent were added for total cell lysis and nucleic acid precipitation. Then RT and real time PCR for IL-1β, IL-1RA and β-actin mRNAs were performed in one step as described in the present invention. Results are expressed in mRNA copy numbers per million of β-actin mRNA copies. The mean and standard error on the mean of five independent experiments are shown.

FIG. 17. Linear regression: mRNA copy numbers on starting blood volume. Various whole blood volumes (ranging from 20 to 200 μl, X-axis) were cultured in the presence of 10 ng/ml LPS for six hours. At the end of the culture, RT and real time PCR for IL-1β and β-actin mRNAs were performed as described in the present invention. The Y-axis represents the raw copy numbers. The line is for linear regression. One experiment representative of six is shown.

Figure 18:
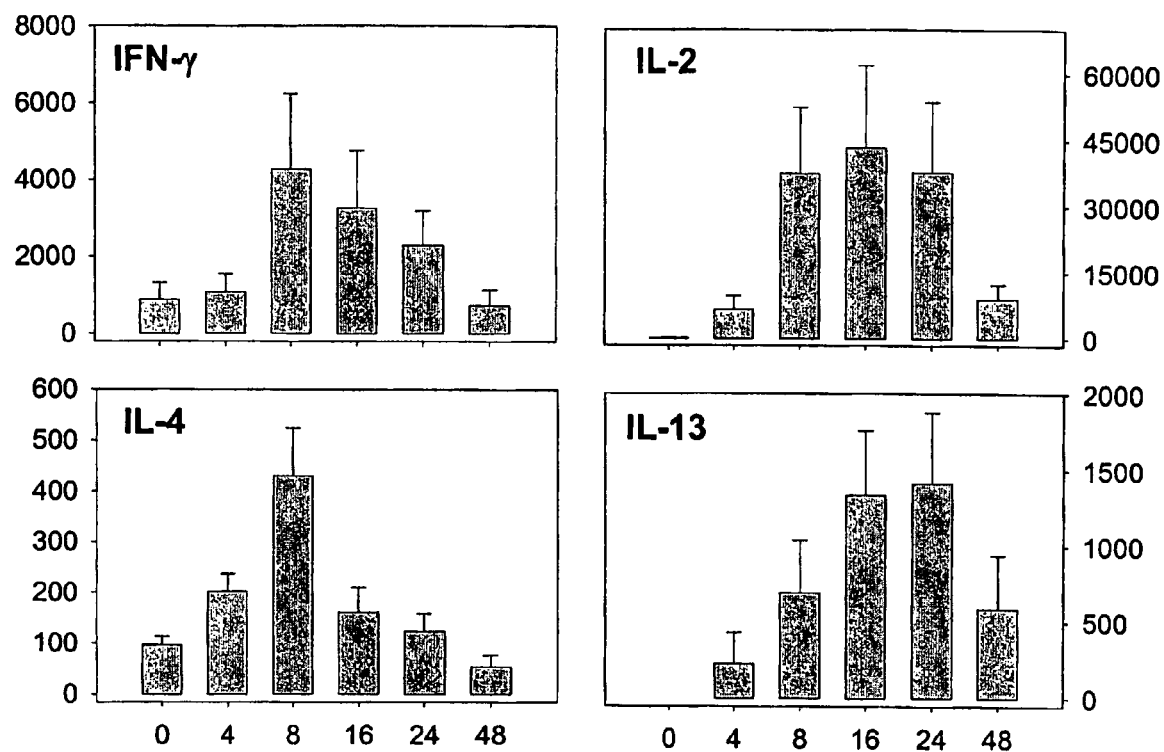

FIG. 18. mRNA cytokine kinetics after whole blood stimulation with tetanus toxoid. Heparinized blood has been taken from five healthy volunteers who were vaccinated against tetanus at least five years ago. For each donor, 200 μl whole blood aliquots were incubated with 10 μg/ml tetanus toxoid for 0 (beginning of the culture), 4, 8, 16, 24 and 48 hours. At the end of the culture, 500 μl of the reagent contained in the PAXgene™ tube were added, and the different transcripts quantified using the methodology of the present invention. Results are expressed in mRNA copy numbers per million of β-actin mRNA copies. The mean and standard error on the mean of five independent experiments are shown.

Figure 19:
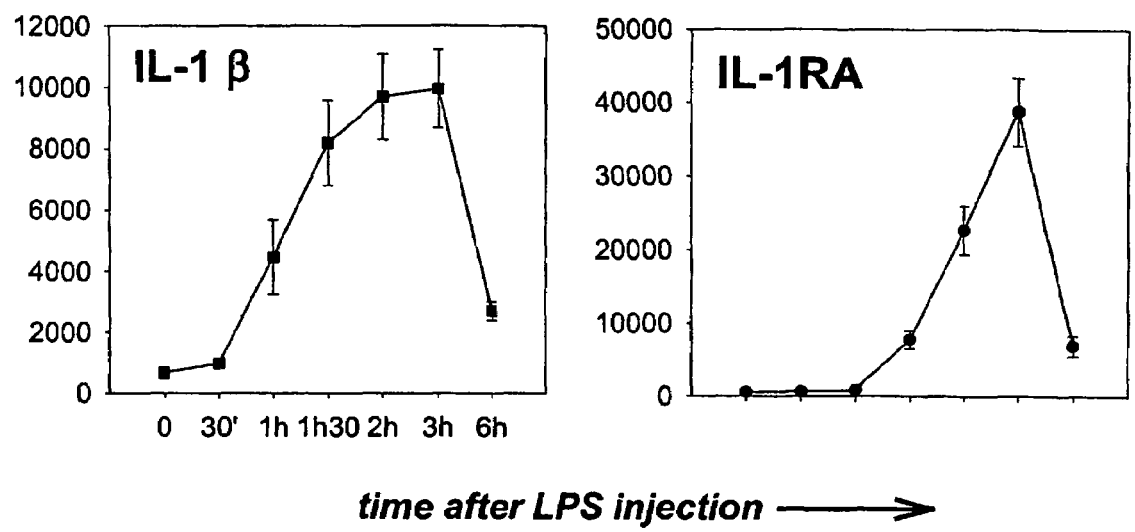

FIG. 19. In vivo modulation of blood cytokine mRNAs after intravenous injection of LPS. Five healthy volunteers were injected with a single dose of 4 ng/kg LPS. Ten minutes before, and 0.5, 1, 1.5, 2, 3 and 6 hours after the LPS injection, a 2.5 ml sample of blood was taken in a PAXgene™ tube. Quantification of cytokine mRNAs was performed according to the method of the present invention. Results are expressed in mRNA copy numbers per million of β-actin mRNA copies. The mean and standard error on the mean for each time point are represented.

Figure 20:
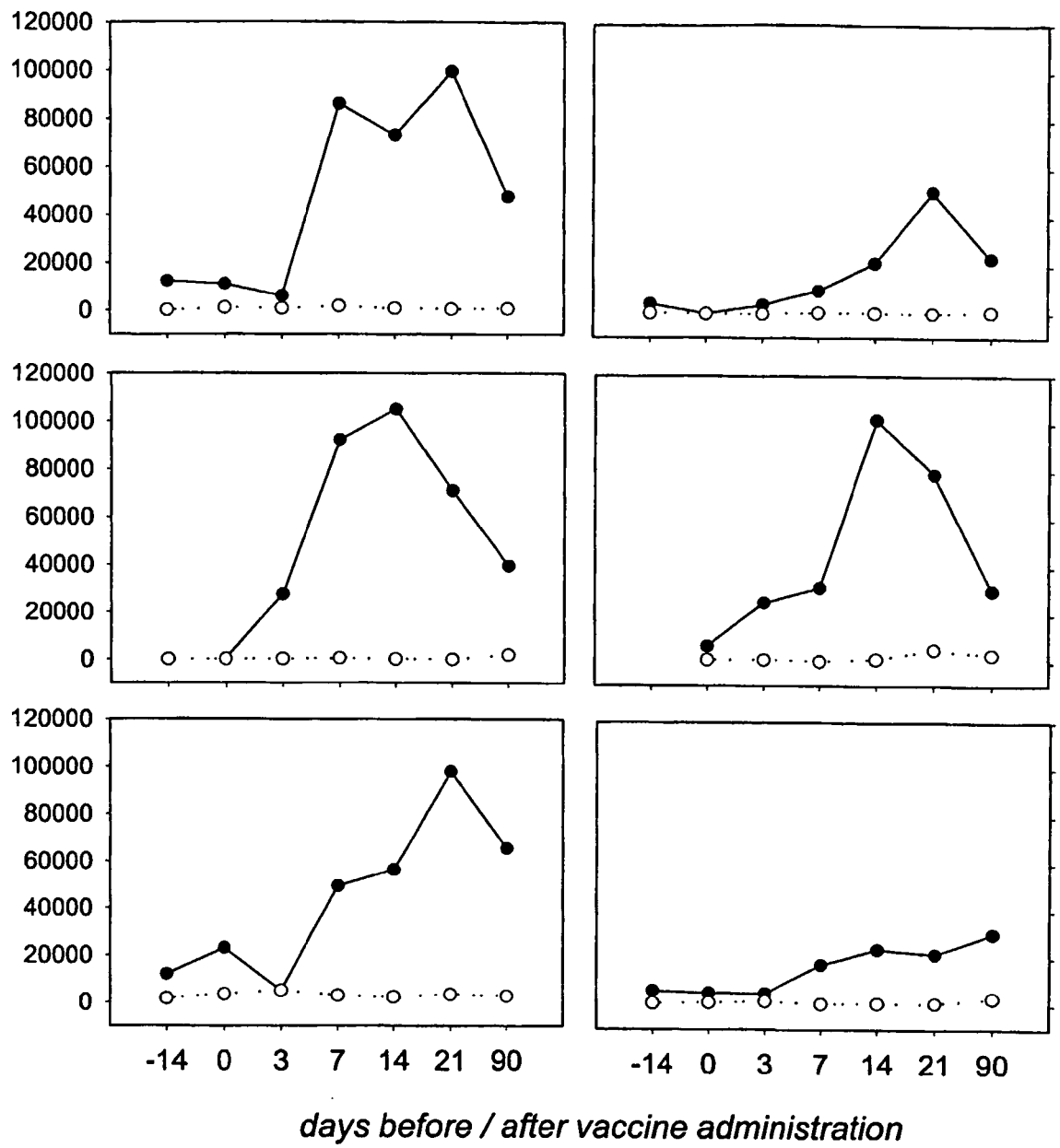

FIG. 20. Follow-up of anti-tetanus vaccine response. Six healthy volunteers were selected to receive an anti-tetanus recall. IL-2 mRNA levels were quantified from whole blood cultured for 20 hours with (full circles) or without (open circles) 10 μg/ml tetanus toxoid, and performed at the moment of the recall (day 0), 14 days before, and 3, 7, 14, 21 and 90 days after (X-axis). Results are expressed in mRNA copy numbers per million of β-actin mRNA copies (Y-axis). Each of the six panels (numbered 1 to 6) represents individual data from 6 different donors (one donor per panel).

FIG. 21. Summary of the procedure followed in examples 7, 8, 9, 10 and 11.

Figure 22:
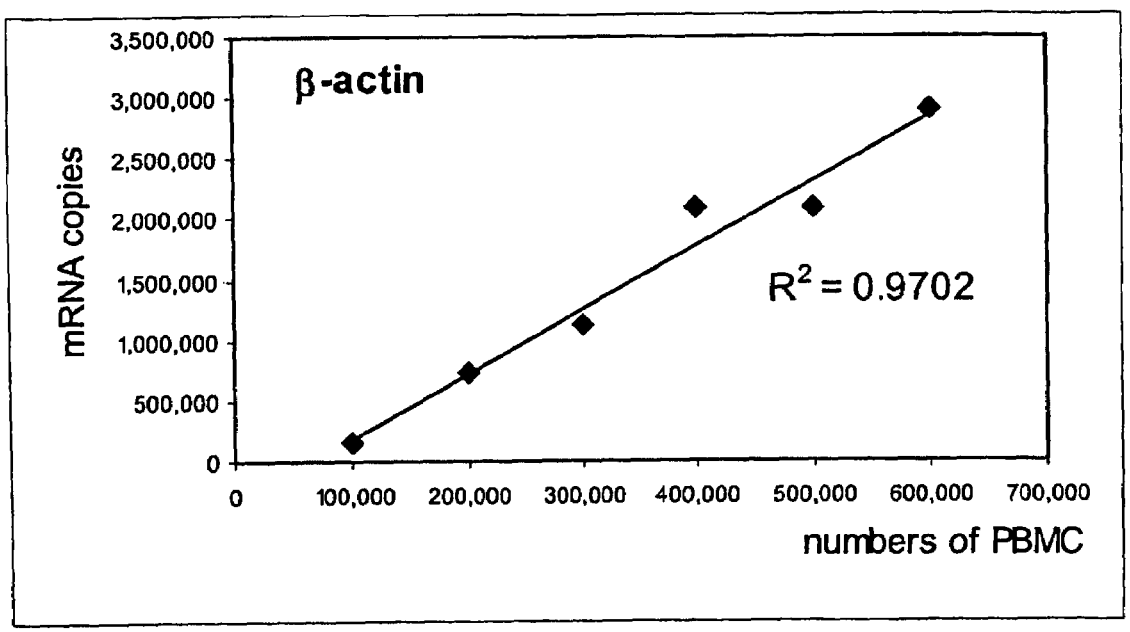

FIG. 22. Automated mRNA extraction and reagent mix preparation on the MagNA Pure. direct correlation between amount of starting biological material and found copy number. The Y-axis represents the raw copy numbers. The line is for linear regression.

Figure 23:
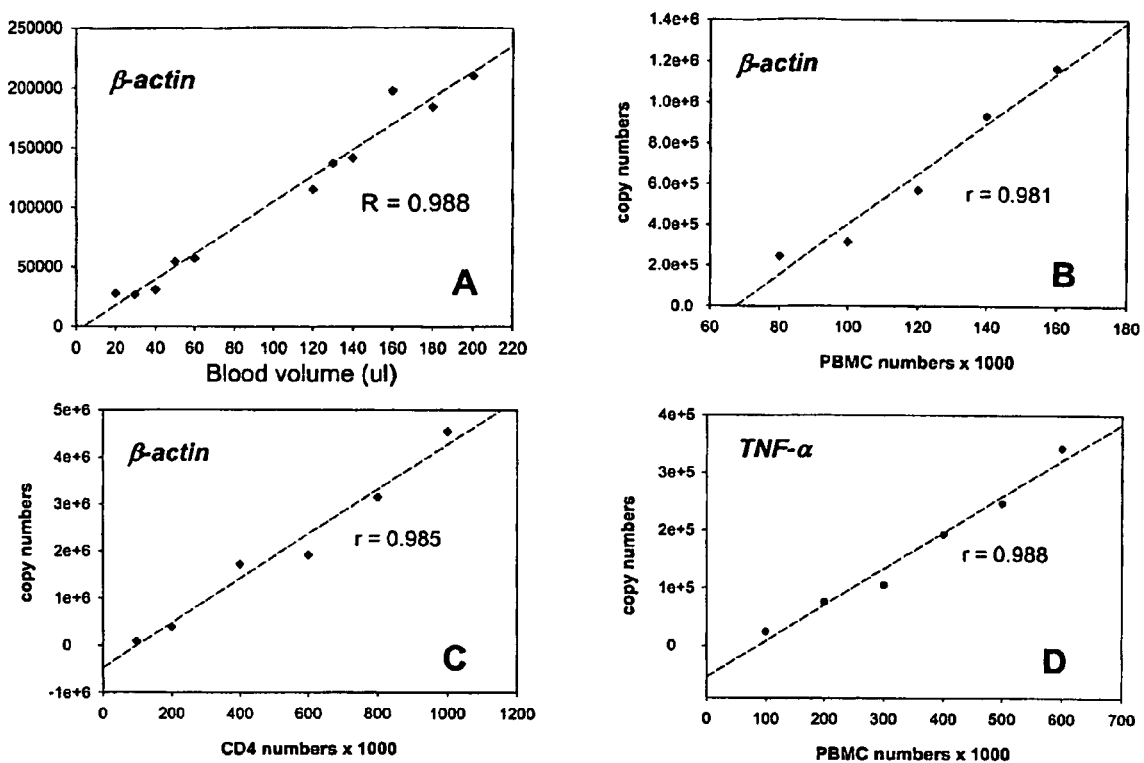

FIG. 23. Automated mRNA extraction and reagent mix preparation on the MagNA Pure. direct correlation between amount of starting biological material and found copy number The Y-axis represents the raw copy numbers. The line is for linear regression.

FIG. 24. Summarised case report of the patient enrolled for cancer immunotherapy. The melanoma was diagnosed in July 1999. In Augusts 2001, multiple metastasis were evidenced, and directly after an orchydectomy in April 2002, the patient was enrolled for receiving a cancer vaccine. The vaccine consisted in several injections of the MAGE-3 purified protein (an antigen specifically expressed by melanoma cells) in combination with an adjuvant.

Figure 25:
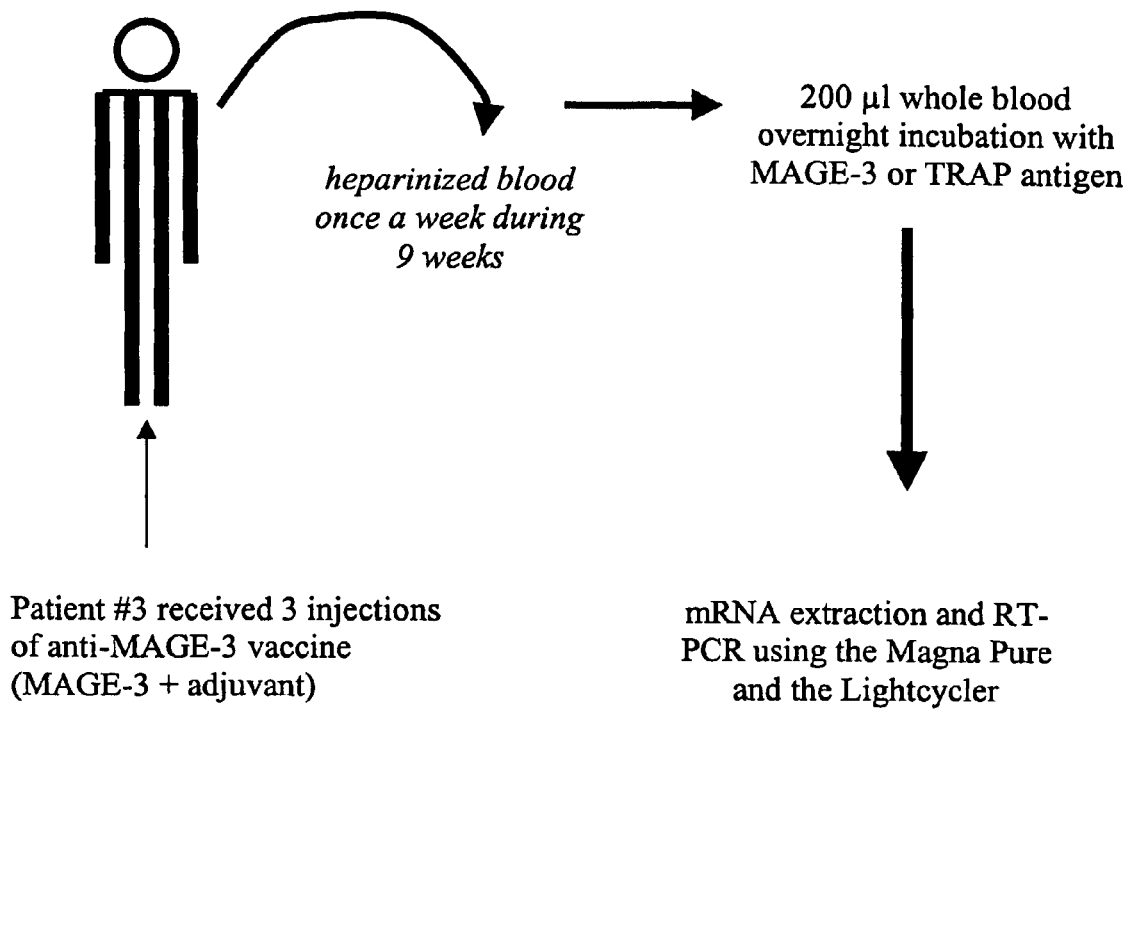

FIG. 25. Schematic representation of the vaccination protocol and the monitoring of immune response by real-time PCR. The patient received 3 injections of the vaccine, while a blood sample was taken once a week during 9 weeks. A 200 μl aliquot of each patient's whole blood sample was incubated in the presence of 10 μg/ml MAGE-3 protein or 10 μg/ml TRAP (*plasmodium falciparum* antigen) as a negative control. At the end of the culture, the reagent contained in the PAXgene tube was added to allow IL-2 mRNA quantification as described in example 6. The results are presented in FIG. 26.

Figure 26:
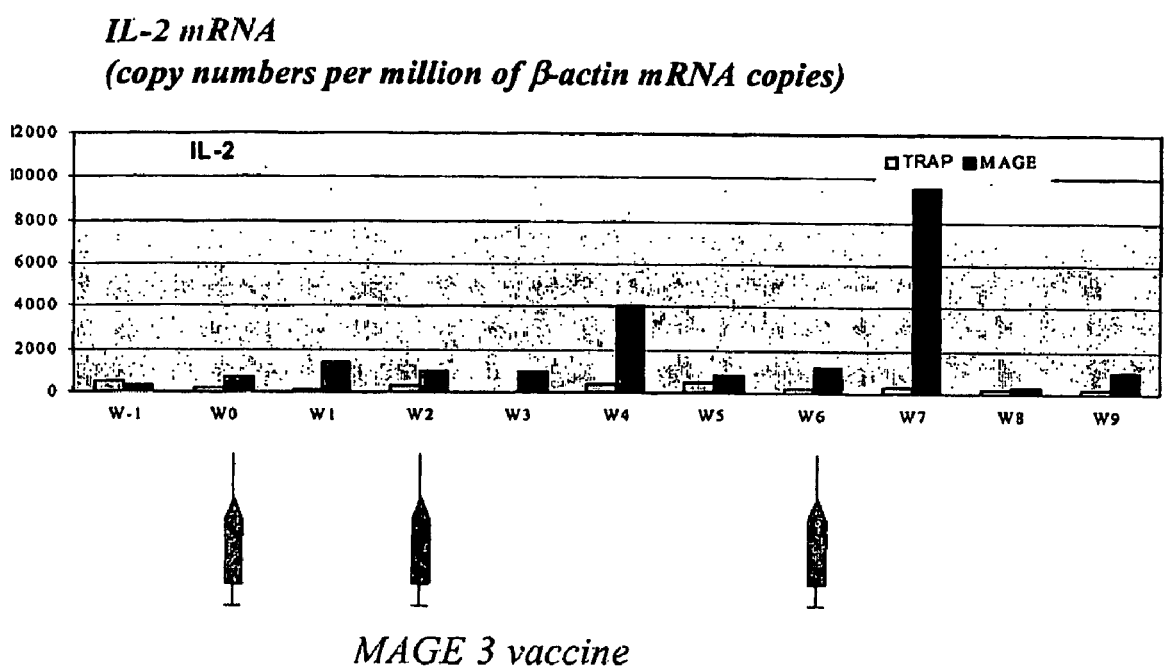

FIG. 26. Higher IL-2 mRNA levels are observed in MAGE-3-stimulated whole blood after MAGE-3 vaccine boost. The Y-axis represents the IL-2 mRNA copy numbers per million of β-actin mRNA copies, and the X-axis the weeks at which blood samples were taken. The vaccine injections were administrated at the weeks 0, 2 and 6. Dark red columns are for whole blood incubated in the presence of MAGE-3, and the blue columns for whole blood incubated in the presence of TRAP.

Figure 27:
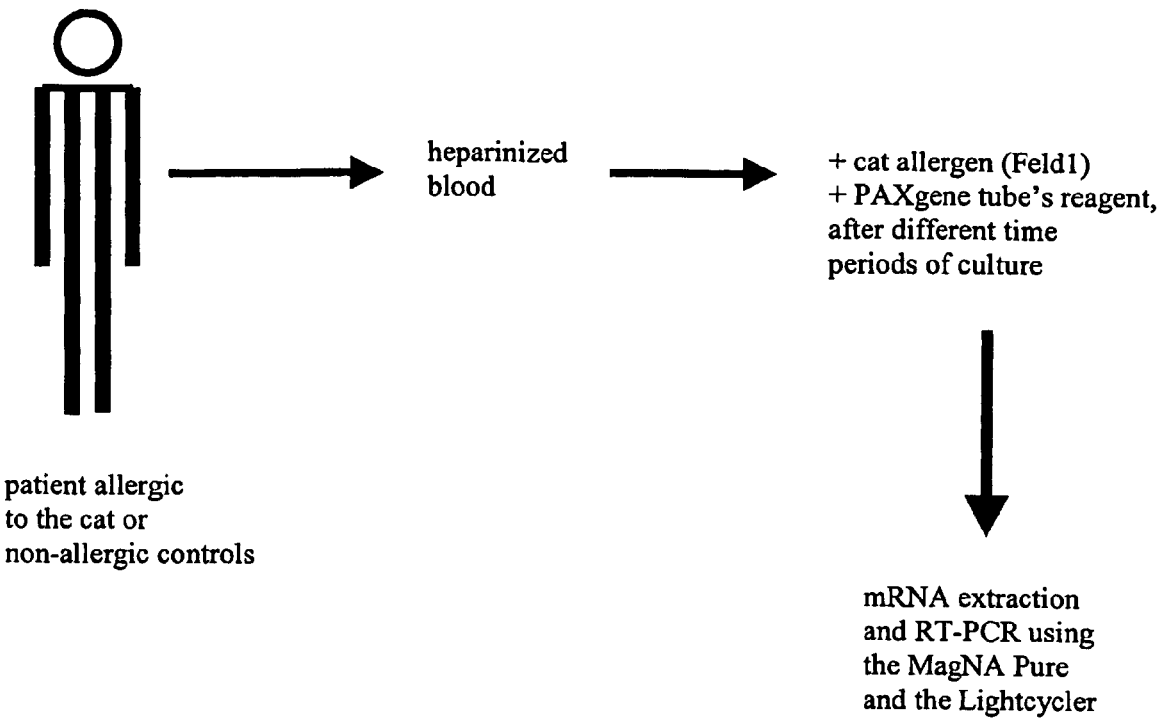

FIG. 27. Schematic representation of the experiment performed for IL-4 mRNA quantification after whole blood incubation with an allergen. Blood samples were taken from a subject allergic to cat, and from two healthy subjects. Whole blood was then incubated in absence or in the presence of the cat allergen (namely Feld1), for different time periods of culture, at the end of which the reagent contained in the PAXgene tube was added to allow IL-4 mRNA quantification as described in example 6. The results are presented on FIG. 28.

Figure 28:
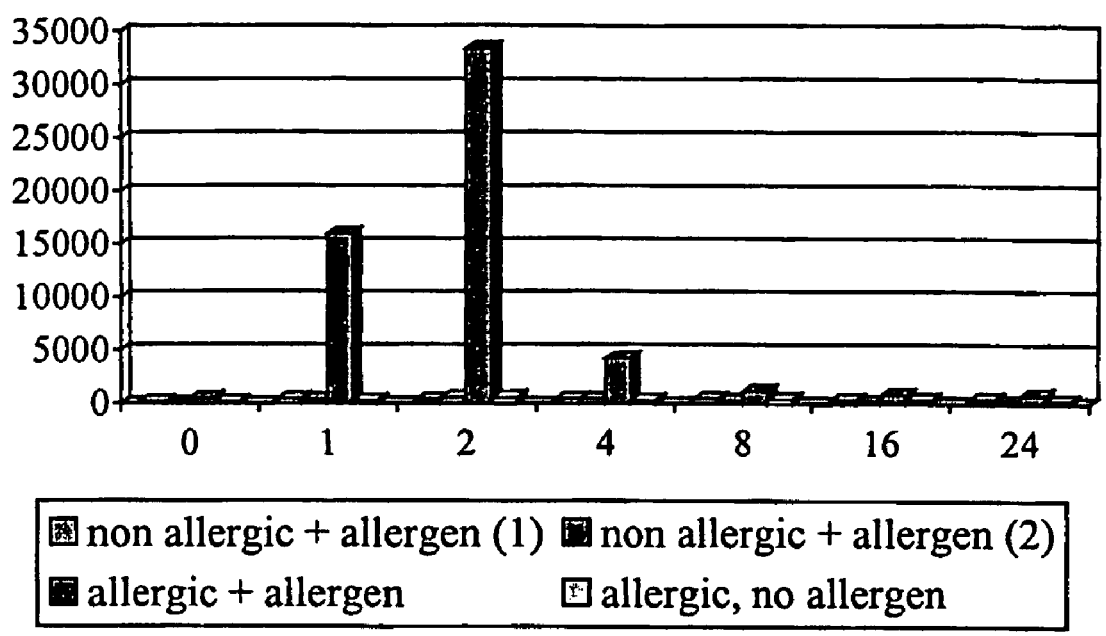

FIG. 28. Feld1 allergen significantly induces higher IL-4 mRNA levels in whole blood coming from the subject allergic to the cat compared to non allergic subjects. The Y-axis represents the IL-4 mRNA copy numbers per million of β-actin mRNA copies, and the X-axis the different incubation times. Green columns represent IL-4 mRNA levels found in normal whole blood incubated with the allergen, IL-4 mRNA levels found in whole blood of the allergic subject being represented by the red columns (blood incubated in the presence of Feld1) and the yellow columns (blood incubated without Feld1).

Figure 29:
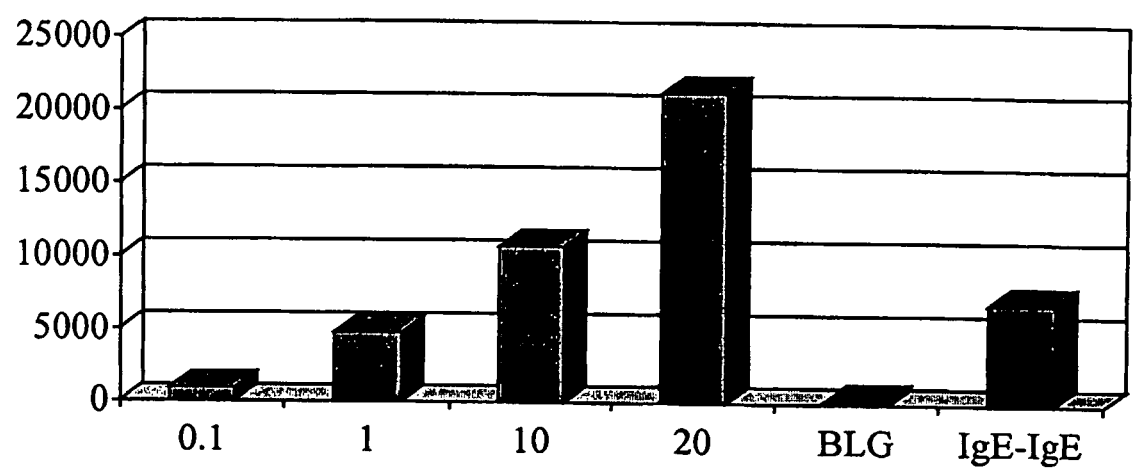

FIG. 29. The response to Feld1 in this whole blood system is specific and dose-related. Whole blood from the allergic subject was incubated for two hours 1) in the presence of increasing concentrations of Feld1 (red columns); 2) in the presence of another allergen, β-lactoglobulin (BLG) at 10 μg/ml (blue column); 3) crossed-linked IgE (green column). The Y-axis represents the IL-4 mRNA copy numbers per million of β-actin mRNA copies.

Figure 30:
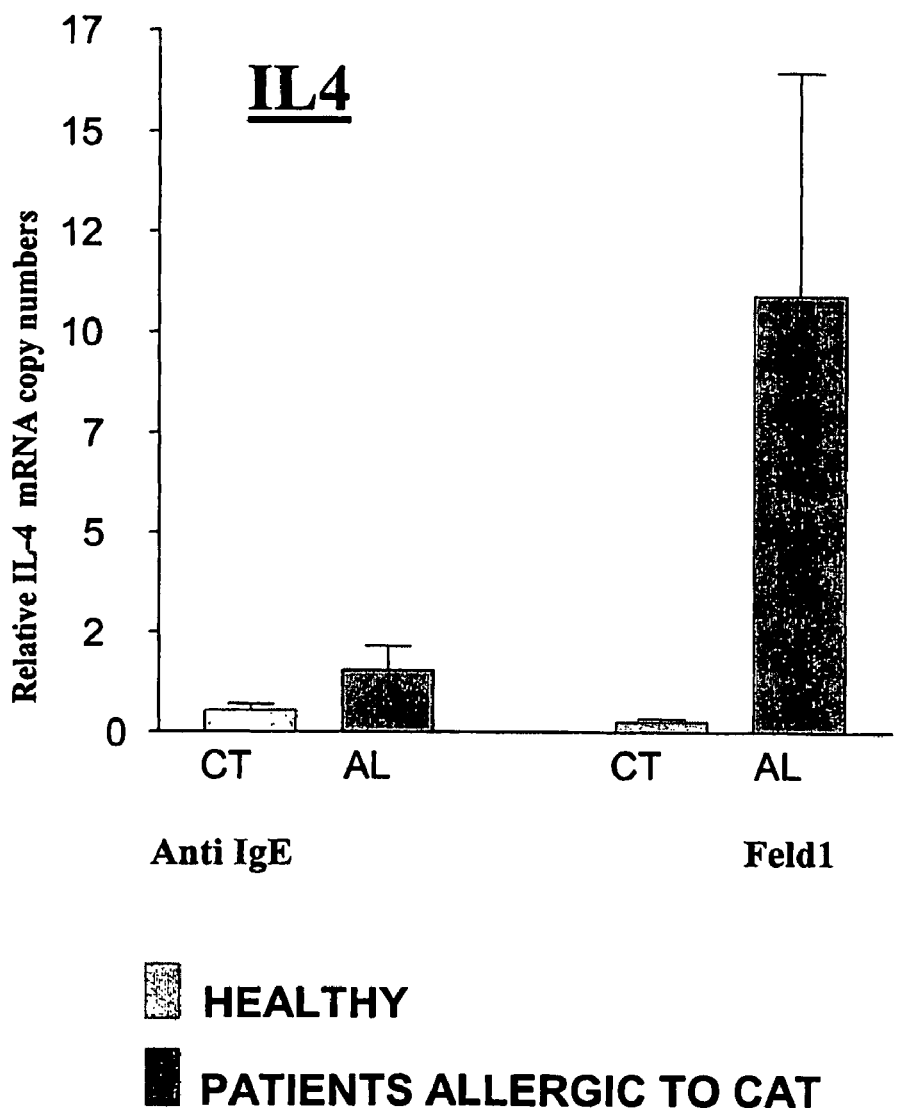

FIG. 30. IL-4 mRNA levels after whole blood stimulation with Feld1 are higher in patients allergic to the cat compared to healthy controls. The experiment described on slides 9 to 11 was repeated on blood samples from 10 healthy subjects (CTR columns) and 10 patients allergic to the cat (ALL columns). Whole blood samples were incubated for two hours in the presence of 10 μg Feld1, or in the presence of crossed-linked IgE as positive controls. The mean and standard error on the mean are represented.

Figure 31:
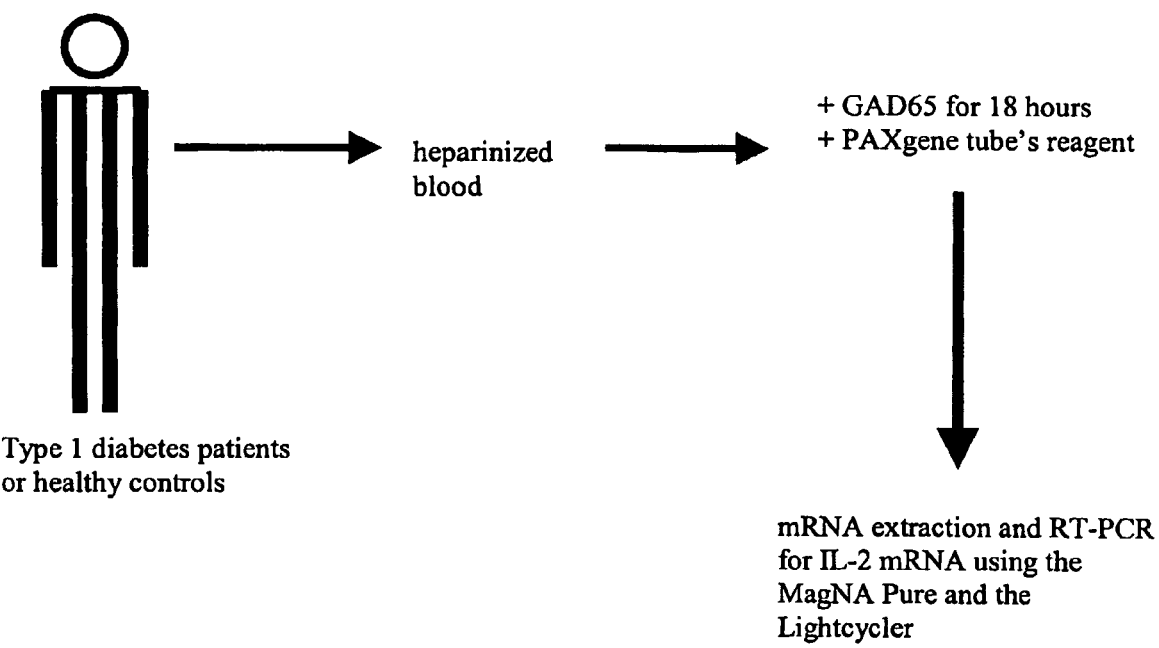

FIG. 31. Schematic representation of the experiment performed for IL-2 mRNA quantification after whole blood incubation with purified GAD65 protein. Blood samples were taken from six type 1 diabetes patients, and from five healthy subjects. Whole blood was then incubated without or with 10 μg/ml GAD65 for 18 hours, the culture being then stopped by adding the reagent contained in the PAXgene tube. IL-2 mRNA levels were then quantified as described in example 6. The results are presented in FIG. 32.

Figure 32:
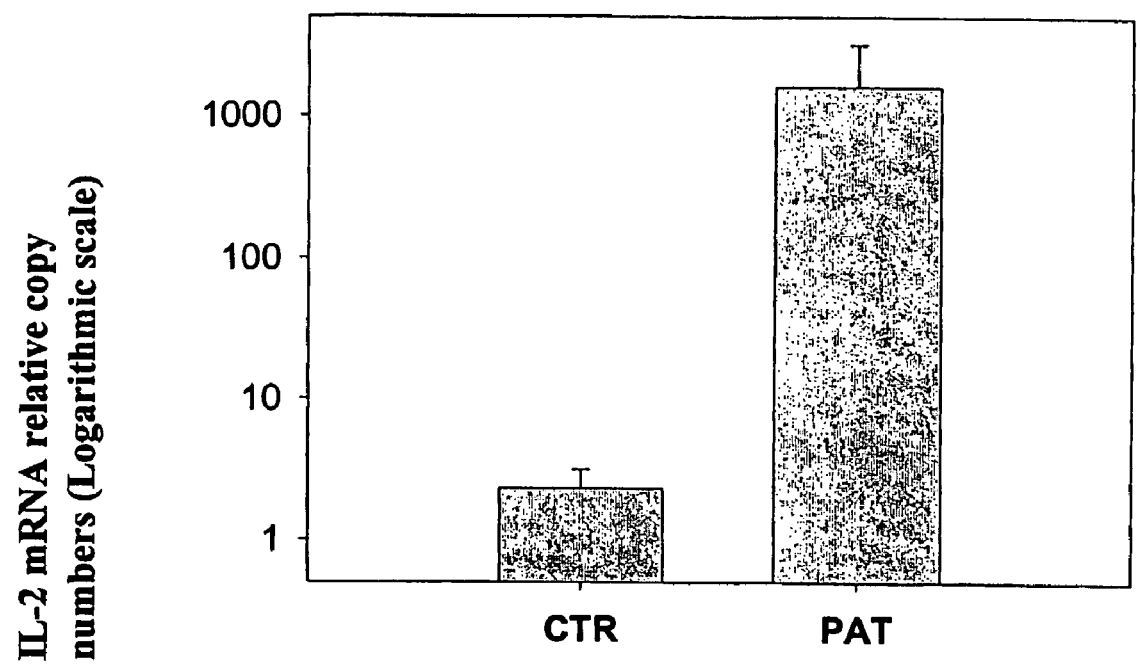

FIG. 32. Whole blood from type 1 diabetes patients shows higher IL-2 mRNA levels after GAD65 stimulation compared to healthy subjects. Results are expressed in IL-2 mRNA copy numbers calculated relatively to the copy numbers found in whole blood cultured without GAD65, after correction against β-actin. A logarithmic scale is used. The mean and standard error on the mean are represented. Healthy donors: CTR column; autoimmune diabetes patients: PAT column.

Figure 33:
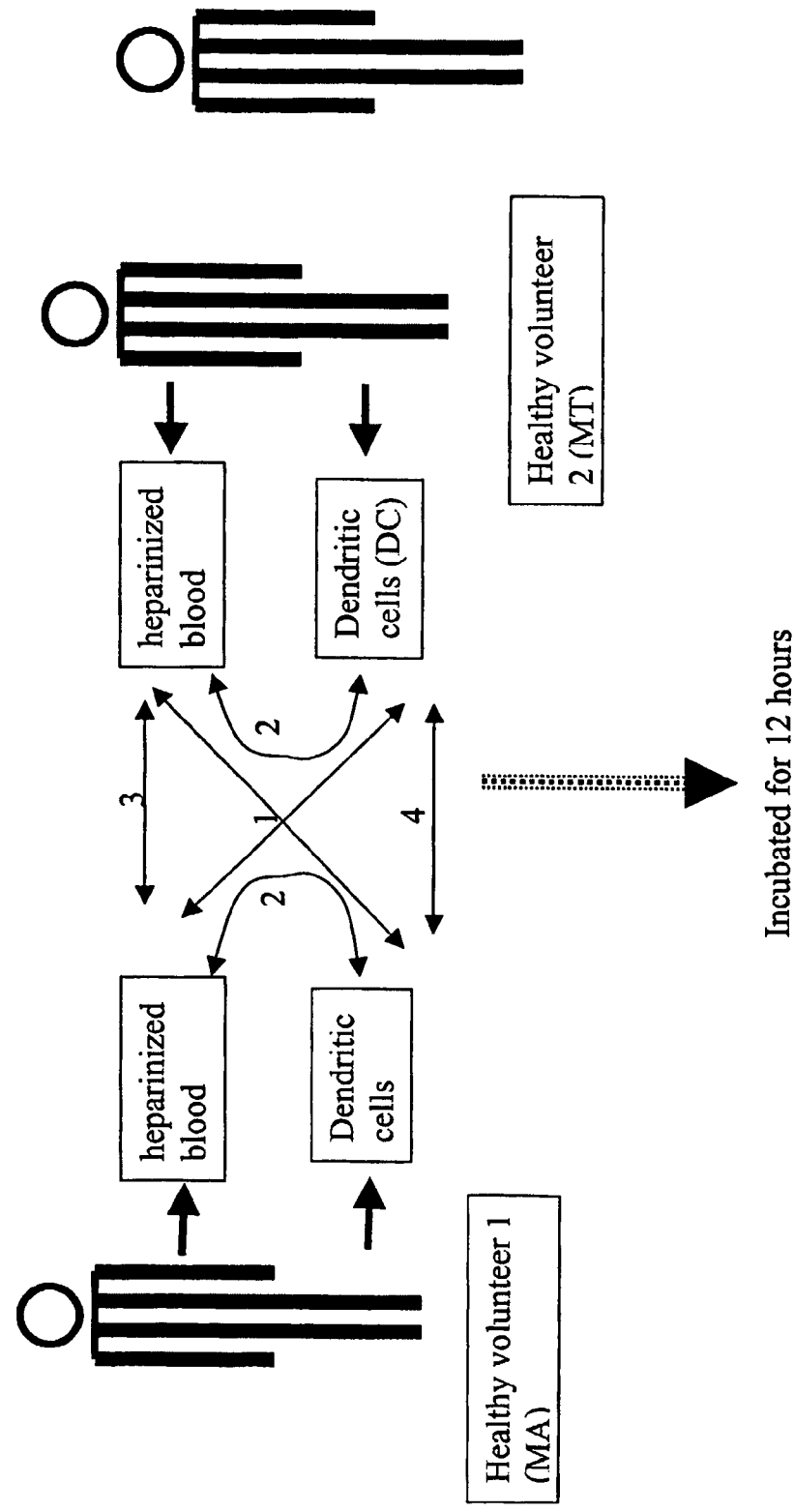

FIG. 33. Schematic representation of the experiment performed for IL-2 mRNA quantification after whole blood incubation with unrelated dendritic cells (DC) to assess alloreactive T cell response. Dendritic cells from two unrelated healthy volunteers (MT and MA) were generated in vitro in the presence of IL-4 and GM-CSF. A whole blood sample from each donor was cultured in the presence of the dendritic cell population of the other donor (1) or in the presence of their own dendritic cells (2). Whole blood samples from both donors were mixed (3), as well as both dendritic cell preparations (4). After 12 hours incubation, the cultures were stopped by adding the reagent contained in the PAXgene tube. IL-2 mRNA levels were then quantified as described in example 6. The results are shown on FIG. 34.

Figure 34:
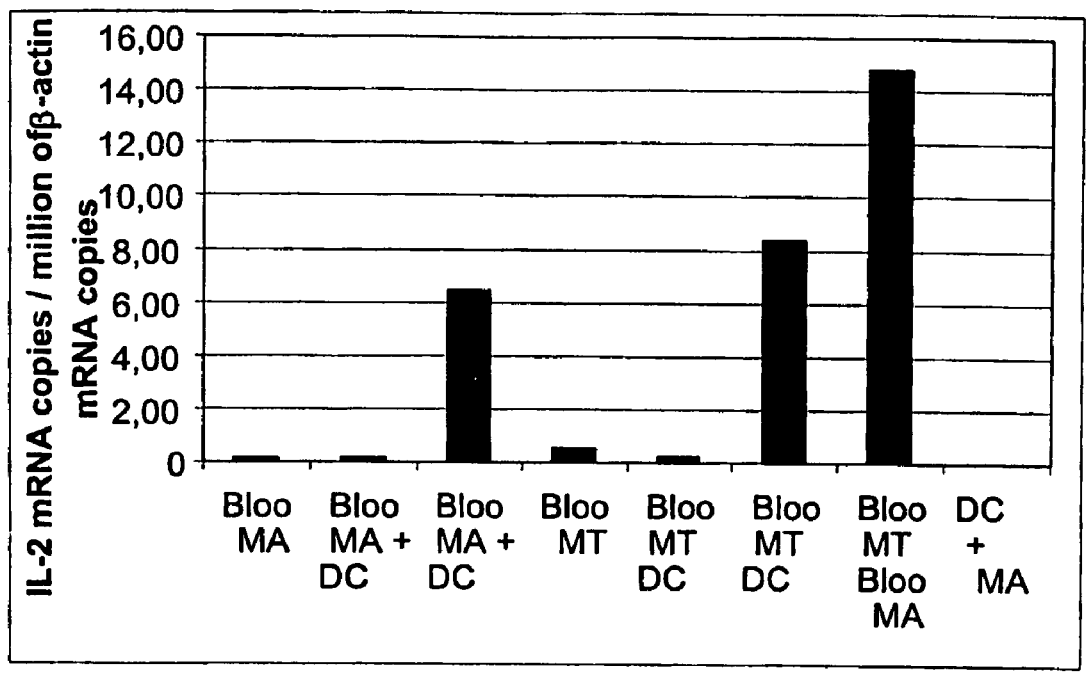

FIG. 34. Assessment of alloreactive T cell response by IL-2 mRNA quantification in whole blood. IL-2 mRNA copy numbers per million of β-actin mRNA copies are shown. The conditions are, from left to right: whole blood from donor MA alone, whole blood from donor MA+DC from donor MA, whole blood from donor MA+DC from donor MT, whole blood from donor MT alone, whole blood from donor MT+DC from donor MT, whole blood from donor MT+DC from donor MA, whole blood from donor MT+whole blood from donor MA, DC from donor MT+DC from donor MA.

EXAMPLES

Example 1

Analysis of Spontaneous Cytokine mRNA Production in Peripheral Blood

The quantification of the cytokine mRNAs synthesized by peripheral blood cells should make it possible to estimate a "peripheral immune statute". However, an accurate quantification can only be performed from a fresh whole blood sample in which mRNA is protected against nuclease digestion, and where gene transcription is inhibited. As discussed in this note, this has been made possible by the use of surfactant reagents such as tetradecyltrimethylammonium oxalate. RT-PCR for the quantification of IL-10 and IFN-γ mRNAs spontaneously produced in peripheral blood was performed. The results showed pronounced higher IFN-γ transcript levels in whole blood compared to peripheral blood mononuclear cells (PBMC) from the same individual, while no significant difference was observed for IL-10 mRNA. The higher amounts of IFN-γ mRNA observed in blood can be attributed at least to mRNA degradation. Using a real time PCR technique, it could indeed be demonstrated that blood IFN-γ mRNA is rapidly degraded in vitro, the t ½ being worth approximately one hour at room temperature.

Härtel et al. recently analysed the influence of cell purification procedure on spontaneous cytokine mRNA production in peripheral blood (Hartel et al., 2001). They showed that freshly isolated peripheral blood mononuclear cells (PBMC) expressed higher levels of IL-2, IL-4 and TNF-α mRNA than freshly collected whole blood from the same individual, while no difference in INF-γ mRNA level was observed. A comparison for INF-γ in six different individuals was performed, and different results were found. A strong expression of INF-γ mRNA in whole blood of all donors was observed, which is clearly decreased in PBMC (FIG. 13.1). This difference between the results obtained and those of Härtel et al, despite the fact that these latter used a quantitative real time PCR technique, could be related to the procedure used to isolate total RNA from whole blood. Härtel et al. used heparinized blood that was hemolyzed within two hours by isotonic ammonium chloride treatment. In the present method tetradecyltrirmethylammonium oxalate was used, a cationic surfactant reagent called Catrimox-14™ (Qiagen, Westburg, Leusden, The Netherlands) that is directly mixed with the blood, avoiding the use of anticoagulants (Dahle and Macfarlane, (1993); Schmidt et al., (1995)). Moreover, this reagent induces nucleic acids precipitation and nuclease inhibition, in the minute that follows sample collection. This provides a total RNA preparation that is probably the nearest of in vivo mRNA status. This is especially important for cytokine mRNA, which are made sensitive to endogenous nucleases by their AU-rich sequences located in their 3' untranslated region. Using a real time PCR technique, it was indeed observed that peripheral blood INF-γ mRNA is spontaneously and rapidly degraded, the levels being decreased by roughly 50% already one hour after blood collection. However, this phenomenon is not necessary true for all the cytokines, as it was found that IL-10 mRNA level is stable for at least the five hours that follow blood sampling (FIG. 13.2). Moreover, no significant differences in whole blood IL-10 mRNA levels were found, compared to those of PBMC (FIG. 13.1).

The nucleic acids pellet obtained after Catrimox-14™ lysis (see legend to FIG. 13.1) can be dissolved in the guanidium/thiocyanate solution described by Chomczynski and Sacchi (1987), as well as in its commercially available version, such as Tripure™ Roche Diagnostics, Molecular Biochemicals, Brussels, Belgium), making the use of this surfactant particularly easy. This means that, except for the first step with Catrimox-1 4™, the RNA isolation procedure is the same for whole blood and cells. Alternatively, PAXgene™ Blood RNA Tubes (Qiagen, Westburg, Leusden, The Netherlands) could be used in the place of Catrimox-14™. In this case, the resulting pellet can be dissolved in the lysis buffer of the "MagNA Pure LC mRNA Isolation Kit I", as described for Catrimox-14™ in legend to FIG. 13.2. The characterisation of spontaneous IL-10 mRNA production by human mononuclearblood cells (Stordeur et al., (1995)), and the monitoring of in vivo tissue factor mRNA induction by OKT3 monoclonal antibody (Pradier et al., (1996)), represent two examples where Catrimox-14 was successfully used. A strong IL-2 mRNA induction was also observed after addition of ionophore A23187+phorbol myristate acetate to whole blood (not shown), suggesting its use for in vitro studies on whole blood.

The observations made in the present example stress the importance to perform RT-PCR from whole blood lysed as fast as possible, in order to accurately quantify peripheral blood cytokine mRNA. For this purpose, the use of reagents such as Catrimox-14 or the additive contained in the PAXgene™ Blood RNA Tubes, together with real time RT-PCR, probably represents to-date the best procedure. By doing so, the study of the natural status of peripheral blood cells would be possible without the use of in vitro strong stimuli such as ionomycin or phytohaemagglutinin.

Example 2

Comparison between the PAXgene™ Blood RNA System and Proposed Method According to the Present Invention With the 'PAXgene™ Blood RNA System' is meant the combination of the PAXgene™ Blood RNA Tube' with the 'PAXgene™ Blood RNA Kit'. With the 'Qiagen Method', it is meant 'PAXgene™ Blood RNA Kit'.

Based on the experimental evidence described in Stordeur et al, J Immunol Methods, 259 (1-2): 55-64, 2002, the present invention proposes a new procedure to isolate mRNA from whole blood which allows to determine in vivo transcript levels using an easy and reproducible method. The PAXgene™ blood RNA System and the method according to present invention are schematically compared in FIG. 14.

Material and Methods:

All experiments were performed from peripheral venous blood directly collected in PAXgene™ Blood RNA Tubes as recommended by the PAXgene™ Blood RNA System (Qiagen) (i.e. 2.5 ml of blood were vacuum collected within the tube that contains 6.9 ml of an unknown reagent). After lysis completion, the content of the tube was transferred in two other tubes: 4.7 ml were used for PAXgene blood RNA kit, and 0.4 ml for MagNA Pure extraction. The remaining of the lysate was discarded. These two tubes were centrifuged at 2,000 g for 10 min and the supernatant discarded. The nucleic acid pellet was then:

a) PAXgene™ Blood RNA Tube+PAXgene™ Blood RNA Kit- . . . washed in water before being dissolved in BR1 buffer for total RNA extraction, as recommended in the corresponding instruction manual. The procedure of the PAXgene™ Blood RNA System is as follows: Blood samples (2.5 ml) are collected in PAXgene Blood RNA Tubes, and may be stored or transported at room temperature if desired. RNA isolation begins with a centrifugation step to pellet nucleic acids in the PAXgene Blood RNA Tube. The pellet is washed, and Proteinase K is added to bring about protein digestion. Alcohol is added to adjust binding conditions, and the sample is applied to a spin column as provided by the PAXgene™ Blood RNA Kit. During a brief centrifugation, RNA is selectively bound to the silica-gel membrane as provided by the PAXgene™ Blood RNA Kit as contaminants pass through. Following washing steps, RNA is eluted in an optimized buffer. Reverse transcription and real time PCR for INF-γ and β-actin mRNAs were conducted as described by Stordeur et al. ("Cytokine mRNA Quantification by Real Time PCR" J Immunol Methods, 259 (1-2): 55-64, 2002).

b) PAXgene™ Blood RNA Tube++MagNA Pure LC mRNA Isolation Kit I- . . . dissolved in 300 µl lysis buffer from the MagNA Pure mRNA Isolation Kit. Extraction and purification of mRNA in a final elution volume of 100 µl were then performed on the MagNA Pure LC Instrument following the instructions from Roche Diagnostics, Molecular Biochemicals. Reverse transcription and real time PCR were conducted in one step, following the standard procedure described in the "Lightcycler—RNA Master Hybridisation Probes Kit" (Roche Diagnostics, Molecular Biochemicals), starting from 5 µl of the mRNA preparation.

Results:

A comparison of the extraction method recommended by Qiagen in combination with the PAXgene™ Blood RNA Tubes (PAXgene™ Blood RNA System), with the MagNA Pure LC Instrument extraction method also in combination with the PAXgene™ Blood RNA Tubes was performed. In both methods the use of the PAXgene™ blood RNA Tubes allows to stabilize RNA from blood cells. The results are listed in Table 1.1 and 1.2. The results of this experiment show a better reproducibility for the MagNA Pure LC Technique (coefficients of variation for IFN-γ mRNA copy numbers corrected against β-actin are 26 versus 16% for Qiagen versus MagNA Pure LC, respectively).

It is interesting to note that MagNA Pure extraction was performed from a starting blood volume lower than that used with the Qiagen method (0.11 ml for MagNA Pure versus 1.25 ml for Qiagen). If the Qiagen method had been performed with such small volume, it would be impossible to measure the RNA concentration, even to perform the reverse transcription. This stresses another advantage of the technique described in the present invention: the possibility to quantify mRNA in a very small volume of blood (about 100 µl).

CONCLUSION

Example 2 illustrates the possibility to use the PAXgene™ Blood RNA Tubes in combination with the MagNA Pure LC mRNA Isolation Kit I, or more precisely, the possibility to dissolve the precipitate from the PAXgene™ Blood RNA Tube in the lysis buffer contained in that kit, this lysis buffer necessarily having to be used with the other components of the kit.

In this example it is proven that in contrast to other combinations, only the combination as described in the present invention, leads to correct/real in vivo transcript quantification.

Example 3

Ex Vivo Monitoring of Immune Response against Tetanus Toxoid

In example 3, blood is stimulated ex vivo with an antigen (i.e. tetanus toxoid) against which the blood donor is supposed to be immunised (because vaccinated seven years ago). RT-PCR is performed according to the method (FIG. 12.1). Cytokine mRNA is measured as a read out of the ability of the volunteer's immune system to react against the antigen. The IL-2, IL-4, IL-13 and INF-γ mRNAs are preferentially analysed, but all potentially reactive proteins can be analysed via the quantification of their corresponding mRNA. Results of example 3 is shown in FIG. 15. Generally the strategy followed in this example can be schematically represented as shown in FIG. 12.2.

Example of Possible Application: Cancer Immunotherapy

Since some years, basic strategies on cancer immunotherapy evolved in the way of the vaccination. In fact, the progresses in genetic and in immunology have allowed identifying a number growing tumor antigens that are expressed to the surface of tumor cells. These antigens are presented to the surface of tumor cells under the form of peptides associated to the major histocompatibility complex (HLA). Example of antigens that might be considered as tumor antigens are described by Fong and Engleman (Annu. Rev. Immunol. 2000. 18:245-273). The principle of the anti-cancer vaccination consists to present these antigens to the system immune of the patient following the most immunogenic way immunogenic. That goes from the injection of the antigen or corresponding peptides in the presence of additives to the presentation of the peptide on autologous antigen presenting cells (dendritc cells, for example). Although the ultimate goal of vaccination anti-cancer vaccination remains the regression of the tumor, the determination of the efficiency of anti-cancer vaccination remains difficult especially in the case of patients in advanced phase of the disease that can profit only from a limited window of treatment. It is the reason why the anti-cancer vaccination could especially be interesting as adjuvant therapy or in the framework of the prevention. It is therefore extremely important to develop sensitive and precise monitoring techniques to evaluate the immunological effects of the experimental anti-cancer vaccination in order to specify the method of administration of these vaccines and discover the implied biological mechanisms that will be able to help better to define the futures therapeutic protocols. The difficulty to measure the immunological efficiency of these vaccines resides essentially in the absence of assays sufficiently sensitive to detect a cellular immune response in vivo. Until now, the used techniques implied the intensive in vitro culture of the PBMC of patients on of long periods times in the presence of antigen and of co-stimulating susceptible to induce a modification of the original functional characteristics of lymphocytes. Thus, the analyses of the anergic states or tolerant states of the lymphocyte precursors directed against the tumor antigens is extremely difficult being given the reversible nature of their functional state after their extended in-vitro incubation in the presence of antigen. On the other side, techniques based on tetramers of MHC-peptides complexes that are used for the detection of low frequencies of epitope-specific-CTL precursors lack usually sensitiveness for the detection of tumor-specific lymphocytes. In addition these techniques do not give any information on the functional reactivity of these lymphocytes Only techniques that are sensitive enough to be able to detect an original functional reactivity of the lymphocytes to a given antigen, for example after a very short stimulation in vitro with antigen will allow a real evaluation of the efficiency of anti-cancer vaccination protocols.

It has been shown recently (Kammula, U. S., Marincola, F. M., and Rosenberg, S. A. (2000) Real-time quantitative polymerase chain reaction assessment of immune reactivity in melanoma patients after tumor peptide vaccination. J. Natl. Cancer Inst. 92: 1336-44) that the detection of cytokine mRNA associated to a short in-vitro stimulation (2 hours) of PBMC were able to detect epitope-specifiq CTLs in the PBMC's of patients undergoing vaccination with a tumor antigen. Nevertheless, according to the present invention this short ex vivo pulse is not essential.

Example 4

Detection of the Activation of the Immune System of the Recipient by the Histocompatibility Antigens of the Donor In example 4, an organ (ex. liver, kidney, bone marrow, etc.) from a donor is transplanted to a recipient. Whole blood the recipient is collected in a tube comprising a compound inhibiting RNA degradation and/or gene induction according to present invention. RT-PCR is performed according to the method. Cytokine mRNA is measured as a read out of the activation of the immune system of the recipient by the histocompatibility antigens of the donor (FIG. 12.3).

Example 5

Detection of the Reactivity of the Immune System of the Recipient to the Histocompatibility Antigens of the Donor In example 5, an organ (ex. liver, kidney, bone marrow, . . . ) from a donor is transplanted to a recipient. Whole blood of the recipient is collected on a tube and incubated ex-vivo with the histocompatibility antigens of the donor. A compound inhibiting RNA degradation and/or gene induction according to present invention is added to the blood. RT-PCR is performed according to the method. Cytokine mRNA is measured as a read out of the response of the immune system of the recipient by the histocompatibility antigens of the donor (FIG. 12.4).

Example of Application: Monitoring of Rejection after Organ Transplantation

The monitoring of rejections of transplants is essentially based on the detection of markers measured in the urine or the blood of patients (blood urea nitrogen-BIN- or creatinine in the case of kidney transplants) or at the time of the analyses of biopsies of the grafted organ. These indicators are however only detected when the rejection mechanism is already well advanced. In fact, transplant rejection is the result of an immunological mechanism that precedes the deterioration of the grafted organ. The detection of these immunological mechanisms before the grafted organ is damaged Would allow to reduce in a considerable manner the loss of the grafted organ by adapting more earlier the immunosuppressive treatments. On the other side, it is also recognized that of subclinical episodes of rejections (with no induction of clinical signs) occur themselves frequently after transplantation. These episodes sub-clinical rejection episodes could be the cause of chronic rejections. Several authors have investigate the detection of precocious immunologiques markers of organ rejection and particularly the detection in the circulation of recipient alloreactive T-lymphocytes directed against the allo-antigens of the donor. Methods include essentially the association of mixed cultures with the consecutive measurement of the proliferation of the lymphocytes of the receiver or the measurement of the production of cytokines by different methods (ELISA, ELISPOT, flow cytometry, etc.). More recently, other authors have looked on the characterization of lymphocytes activation markers patterns susceptible to underline precociously the triggering of a rejection mechanism. The detection of mRNA of genes expressed by the cytotoxic activated T-lymphocytes T activated (granzyme B, perforine, different cytokines) by sensitive methods of quantitative PCR were showed to be excellent tools to measure the triggering of a rejection. For this purpose, according to present invention, messengers coding for different kinds of cytokines may be studied, preferential targets may be IL-2, IFN-gamma, IL-4, IL-5, Granzyme, perforine and FasFas-ligand.

Example 6

Immune Monitoring in Whole Blood Using Real Time PCR

In example 6 a whole blood method is described allowing the measure of the induction of cytokine synthesis at the mRNA level. The originality of this method consists in the combination of PAXgene™ tubes containing a mRNA stabilizer for blood collection, the MagNA Pure™0 instrument as an automated system for mRNA extraction and RT-PCR reagent mix preparation, and the real time PCR methodology on the Lightcycler™ for accurate and reproducible quantification of transcript levels. This example first demonstrate that this method is adequate to measure the induction of IL (interleukin)-1β and IL-1 receptor antagonist (IL-1 RA) mRNA upon addition of bacterial lipopolysaccharide (LPS) to whole blood. This example further demonstrates that this approach is also suitable to detect the production of mRNA encoding T cell-derived cytokines in whole blood incubated with tetanus toxoid as a model of in vitro immune response to a recall antigen. Finally, the example demonstrates that this methodology can be used successfully to assess inflammatory as well as T cell responses in vivo, as it allowed to detect the induction of IL-1β and IL-1 RA after injection of LPS in healthy volunteers, and also the induction of IL-2 upon recall immunisation with tetanus vaccine.

Material and Methods.

Blood collection for in vivo studies. For accurate quantification of peripheral blood mRNA levels, a 2.5-ml sample of blood was taken in a PAXgene™ tube for immediate cell lysis and nucleic acid precipitation. The mRNA is stable for up to 5 days in this blood lysate, the tubes being kept at room temperature until mRNA extraction.

In vitro whole blood culture. In vitro whole blood LPS stimulation or tetanus toxoid rechallenge were performed on 200 μl of heparinized whole blood, and started at the latest four hours after blood collection. Cultures were stopped by adding 500 μl of the PAXgene™0 tube's reagent, which induces total cell lysis and mRNA stabilisation. This allowed the use of the same mRNA extraction protocol for both in vitro and in vivo studies.

mRNA extraction. The blood lysate obtained in the PAXgene™ tube or at the end of whole blood culture was briefly mixed before transferring a 300-μl aliquot in a 1.5-ml eppendorf tube for centrifugation at maximal speed for 5 minutes (12,000 to 16,000 g, depending on the device). The supernatant was discarded, and the nucleic acid pellet thoroughly dissolved by vortexing in 300 μl of the lysis buffer contained in the MagNA Pure™ mRNA extraction kit (Roche Applied Science). mRNA was then extracted from 300 μl of this solution, using this kit on the MagNA Pure™ instrument (Roche Applied Science) following manufacturer's instructions ("mRNA I cells" Roche's protocol, final elution volume 100 μl). The quality of the extracted mRNA was previously documented by Northern blot analysis (Roche Applied Science, unpublished data).

Real time PCR and reagent mix preparation. Reverse transcription and real time PCR were performed in one step, following the standard procedure described in the "Lightcycler™—RNA Master Hybridisation Probes" Kit (Roche Applied Science). More precisely, the RT-PCR reaction was carried out in a 20 μl final volume containing: 1) $H_2O$ up to 20 μl; 2) 7.5 μl RNA Master Hybridisation Probes 2.7× conc (RNA Master Hybridisation Probes Kit—Roche Applied Science); 3) 1.3 μl 50 mM Mn $(OAc)_2$; 4) 1, 2 or 3 μl of 6 pmoles/μl forward and reverse primers (final concentration 300, 600 or 900 nM, depending of the mRNA target; the conditions specific for each mRNA target are fully described in Stordeur et al, J Immunol Methods, 259 (1-2): 55-64, 2002, excepted for IL-2 and IL-4, which are listed in Table 2); 5) 1 μl of 4 pmoles/μl TaqMan probe (final concentration 200 nM); 6) 5 μl purified mRNA or standard dilution. After an incubation period of 20 minutes at 61 ° C. to allow mRNA reverse transcription, and then an initial denaturation step at 95° C. for 30 s, temperature cycling was initiated. Each cycle consisted of 95° C. for 0 (zero) second and 60° C. for 20 s, the fluorescence being read at the end of this second step (F1/F2 channels, no colour compensation). 45 cycles were performed, in total. All primers were chosen to span intronic sequences, so that genomic DNA amplification was not possible.

The RT-PCR reaction mixtures containing all reagents, oligonucleotides and samples, were fully prepared directly in the capillaries used on the Lightcycler™, by the MagNA Pure™ instrument. These capillaries were top closed, centrifuged and then introduced in the Lightcycler™ for one step RT-PCR. The sampling of all RT-PCR components was thus fully automated, avoiding manual sampling errors.

Results were expressed in copy numbers normalised against β-actin mRNA (mRNA copy numbers of cytokine mRNA per million of β-actin mRNA copies). For each sample, the mRNA copy number was calculated by the instrument software using the Ct value ("Arithmetic Fit point analysis") from a standard curve. This latter was constructed for each PCR run from serial dilutions of a purified DNA, as described in Stordeur et al, J Immunol Methods, 259 (1-2): 55-64, 2002.

Experimental endotoxemia. Five healthy male volunteers (21-28 years) who had not taken any drugs for at least 10 days before the experiments were received an intravenous injection with a single dose of LPS (from *E. coli*, lot G; United States Pharmacopeial Convention, Rockville, Md.; 4 ng/kg body weight). Ten minutes before, and 0.5, 1, 1.5, 2, 3 and 6 hours after the LPS injection, a 2.5 ml sample of blood was taken in a PAXgene™ tube. For in vitro studies, 200 μl of heparinized whole blood taken from healthy individuals were incubated with 10 ng/ml LPS (from *E. coli* serotype 0128: B12, Sigma-Aldrich, Bornem, Belgium) for 0 (beginning of the culture), 0.5, 1, 2 and 6 hours, at 37° C. in a 5% $CO_2$ atmosphere.

Anti tetanus recall vaccination. Healthy volunteers (2 males, 4 females, 27-53 years) whom last tetanus toxoid vaccination was at least five years ago, received an intra muscular vaccine recall (Tevax, Smith Kline Beecham Biologicals, Rixensart, Belgium). A heparinized blood tube was taken the day of administration, 14 days before, and 3, 7, 14, 21 and 90 days after. 200 μl of blood were incubated, at 37° C. in a 5% $CO_2$ atmosphere, with or without 10 μg/ml tetanus toxoid (generous gift from Dr. E. Trannoy, Aventis Pasteur, Lyon, France) for 20 hours.

Results

Measurement of IL-1β and IL-1 RA mRNA upon addition of bacterial LPS to whole blood. As demonstrated in FIG. 16, addition of LPS (10 ng/ml) to whole blood led to a rapid induction of IL-1β and IL-1 RA mRNAs. This induction, already evident 30 to 60 minutes after LPS addition, resulted 6 hours after in a 47-fold and a 22-fold increase of the mRNA levels for IL-1β and IL-1 RA, respectively. The pattern of the curves suggests a rapid and sustained increase of both cytokine mRNAs amounts. In order to evaluate the accuracy of the system for mRNA quantification, the mRNA was quantified for β-actin and IL-1β from different volumes of LPS-stimulated whole blood, ranging from 20 to 200 µl. As shown in FIG. 17, the mRNA copy numbers of both β-actin and IL-1β were indeed directly correlated with the starting volume of blood.

In vitro response to tetanus toxoid. To determine whether this method might be suitable for the analysis of T cell responses, cytokine mRNA levels in whole blood culture after addition of tetanus toxoid, a well established recall antigen as all individuals were vaccinated in childhood, was quantified. A rapid and transient induction of IFN-γ, IL-2, IL-4 and IL-13 mRNA after incubation of whole blood with this antigen was found (FIG. 18). When comparing the amplitude of the response for each cytokine, it appeared that the induction of IL-2 mRNA was the most pronounced. Indeed, the global increase of IL-2 mRNA copies after 16 hours of incubation in the presence of the toxoid was around 220 fold for the five independent experiments shown in FIG. 18, while the maximum increase of IL-4 and IFNγ mRNAs in the same experiments did not exceed 5 fold. Quantification of IL-2 mRNA therefore appears as the most sensitive parameters in this whole blood system assessing T cell responses. Data given in Table 3 indicates that the amplitude of the response to tetanus toxoid in this test is rather variable, probably depending on the moment of the last vaccine recall. The induction of IL-2 mRNA was effectively not observed after addition of tetanus toxoid to neonatal cord blood, indicating that only previously primed T cells and not naive T cells are able to respond in this assay (Table 3).

Induction of IL-1 RA and IL-1β mRNA in whole blood after intravenous injection of LPS. As a first application of the method for the detection of cytokine induction in vivo, serial blood samples from healthy volunteers injected with a low dose (4 ng/kg) of bacterial lipopolysaccharide was analysed. A clear induction of both IL-1 RA and IL-1β mRNA was observed (FIG. 19). The induction of IL-1β mRNA was rapid, since it was already detected 30 to 60 minutes after endotoxin administration, and transient as IL-1β mRNA levels returned to pre-injection values after 6 hours. IL-1 RA mRNA was also induced, with a delayed kinetics as compared to IL-1β mRNA.

Detection of anti-tetanus toxoid immune response after recall vaccination. As the in vitro experiments suggested that IL-2 mRNA was the most sensitive parameter to monitor anti-tetanus toxoid responses, this parameter was chosen to analyse the changes in the T cell responses to tetanus toxoid in whole blood upon recall vaccination in vivo. For this purpose, whole blood incubation in absence or presence of tetanus toxoid was performed before and at several time points after administration of the vaccine. As shown in FIG. 20, the production of IL-2 mRNA in whole blood exposed to the antigen significantly increased in all vaccinated individuals. IL-2 mRNA induction was already apparent 7 days post vaccination, maximal levels being reached at day 14 or 21. The variability between individuals is probably related to differences in the basal status of anti-tetanus immunity (see also Table 3). The IL-2 response measured in whole blood after vaccination was specific for the immunising antigen as IL-2 mRNA levels measured in absence of in vitro restimulation were not significantly modified (Table 3).

Discussion

Real time PCR is so called because the amplicon accumulation can be directly monitored during the PCR process, using fluorogenic molecules that bind the PCR product. This leads to the generation of a fluorescence curve for each sample, from which it is possible to determine the (c)DNA copy number of the sample, by comparison to fluorescence curves obtained with calibrated standards. In order to enhance the specificity, the fluorogenic molecule can be an oligonucleotide complementary to a sequence of the PCR product, localised between the two primers. The new methodology, as described in the present application, provides a sensitive and accurate way to quantify nucleic acids in biological samples which was not possible using the prior art methods. The present application illustrates this by quantifying cytokine mRNA from purified cells or tissues representative of the in vivo situation.

One of the difficulties encountered using whole blood for RT-PCR analysis is the cell lysis that precedes RNA extraction. Because of the high amount of proteins present in plasma and erythrocytes, the majority of the methods that isolate RNA from whole blood involve the purification of the potential cellular sources of the analysed mRNA or the elimination of the red blood cells, before performing the RNA extraction. These intermediate steps can be associated with mRNA degradation and/or gene induction and thus with changes in mRNA levels. Furthermore, the simple fact of taking blood can lead to degradation of some mRNAs. This is especially true for cytokine mRNAs, which are sensitive to endogenous nucleases via the AU-rich sequences located in their 3' untranslated region. It was previously shown that peripheral blood IFN-γ mRNA levels indeed decreased by roughly 50% already one hour after blood collection (Stordeur et al., (2002) J. Immunol Meth. 261:195). This can be avoided using quaternary amine surfactants such as tetradecyltrimethylammonium oxalate, a cationic surfactant called Catrimox-14™ (Qiagen, Westburg, Leusden, The Netherlands) that induces whole cell lysis and, in the same time, nucleic acid precipitation. The present example observes that the nucleic acid precipitate obtained with the PAXgene™ tubes can surprisingly be dissolved in a guanidium/thiocyanate solution. An example of said solution is the lysis buffer provided with the MagNA Pure ™ LC kits for mRNA isolation (Roche Applied Science). This prompted us to combine the use of PAXgene™ tubes with the MagNA Pure™ instrument, taking advantage of the high reproducibility and accuracy of the latter device due to the automated preparation of all of the components of the PCR reaction mixture.

Interestingly, the method of the present application was successfully applied to the detection of cytokine gene induction in whole blood upon endotoxin challenge in vivo, demonstrating that it could be used to monitor systemic inflammatory responses, The transient nature of the IL-1 response after in vivo challenge, contrasts with the persistent increase in IL-1 mRNA after in vitro addition of LPS to blood. This might be related to the rapid clearance of LPS in vivo but also to the redistribution of cytokine-producing cells in vivo, which is related to upregulation of adhesion molecules and chemokine receptors. Another possible application of this whole blood method is the monitoring of T cell responses upon vaccination, as suggested by the clear induction of IL-2 mRNA observed after in vitro rechallenge in individuals vaccinated with tetanus toxoid. This might be of special interest for large-scale vaccination studies in which cell isolation might be difficult to organise in good conditions, especially in developing countries where several new vaccines are under evaluation. To further investigate the applicability of this method in vaccine trials, it will be soon tested as read-out of T cell responses upon primary vaccination against hepatitis B.

The direct correlation between the starting volume of blood and the mRNA copy numbers (FIG. 17) suggests that there is no absolute need to measure mRNA concentration for expression of the results using this method. However, because even small variations of the sample volume could result in quantfication errors, it is preferable to correct the measured copies by simultaneous measurement of a housekeeping gene such as β-actin. This might still not be optimal as the expression of housekeeping genes might vary in certain conditions of stimulation. Therefore an external standard could be added to the sample before mRNA extraction. When the cellular source of a cytokine is well established such as in the case of T cells for IL-2, it might be appropriate to correct the numbers of cytokine gene copies by the numbers of copies encoding a gene specifically expressed in the corresponding cell type, such as CD3 in the latter example. Likewise, international standardisation of calibrators for cytokine mRNA quantification by real time PCR should be developed to facilitate comparison of data generated in different laboratories. Cytokine mRNA measurement in whole blood is useful for the monitoring of innate and adaptive immune responses required for the assessment of new vaccines and immunotherapies.

Example 7

Automated mRNA Extraction and Reagent Mix Preparation on the MagNA Pure: Direct Correlation between Amount of Starting Biological Material and Found Copy Number The procedure followed in this example is summarized in FIG. 21. In order to illustrate the accuracy of the system, a linear regression of mRNA copy number on starting cell number was calculated (FIG. 22). mRNA was extracted from various peripheral blood mononuclear cell (PBMC) numbers (ranging from 100,000 to 600,000 cells, X-axis) and one step RT-real time PCR for β-actin mRNA was performed as described in the "Material and Methods" section of the present example 6. This experiment has been repeated from PBMC for β-actin and TNF-α mRNAs (FIG. 23, panels B and D), and from whole blood (FIG. 23, panel A) and CD4+ purified T cells (FIG. 23, panel C) for β-actin mRNA.

Example 8

Cancer Immunotherapy

The procedure followed in this example is summarized in FIG. 21. The methodology was applied to the monitoring of immune response induced by cancer vaccine. FIGS. 24, 25 and 26 illustrate the results obtained in this field with a melanoma patient.

Example 9

Allergy

The procedure followed in this example is summarized in FIG. 21. The methodology was then applied in Allergy. The response induced by in vitro incubaton of whole blood of an allergic subject with the relevant allergen was analysed by IL-4 mRNA quantification using real-time PCR. FIGS. 27, 28, 29 and 30 illustrate the results obtained in this field.

Example 10

Autoimmunity

The procedure followed in this example is summarized in FIG. 21. The methodology was then applied in Autoimmunity. IL-2 mRNA quantification using this whole blood system was applied to assess T cell response to glutamic acid decarboxylase 65 (GAD65), an autoantigen being the target of auto-reactive T cells in type 1 autoimmune diabetes. FIGS. 31 and 32 illustrate the results obtained in this field.

Example 11

Transplantation

The procedure followed in this example is summarized in FIG. 21. The methodology was then applied in Transplantation. IL-2 mRNA quantification by real time PCR after whole blood incubation with alloreactive non-T cells provides an alternative to the classical mixed lymphocytes reaction (MLR) to monitor alloreactve T cell response. FIGS. 33 and 34 illustrate the results obtained in this field.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

TABLE 1

Comparison of Qiagen and MagNA Pure LC extraction methods.

IFN-gamma mRNA copy numbers per million of beta-actin mRNA copies

| 1.1. Qiagen mRNA extraction method. Blood mRNA coming from the same blood sample was extracted 9 times. | |
| --- | --- |
| result 1 | 35 |
| result 2 | 25 |
| result 3 | 29 |
| result 4 | 27 |
| result 5 | 27 |
| result 6 | 49 |
| result 7 | 33 |
| result 8 | 22 |
| result 9 | 27 |
| mean | 30 |
| SD | 8 |
| CV | 26 |

| 1.2. MagNA Pure LC (kit + instrument) mRNA extraction method. Blood mRNA prepared from the same blood sample was extracted 9 times. | |
| --- | --- |
| result 1 | 192 |
| result 2 | 170 |
| result 3 | 153 |
| result 4 | 139 |
| result 5 | 138 |
| result 6 | 160 |
| result 7 | 105 |
| result 8 | 142 |
| result 9 | 142 |
| mean | 149 |
| SD | 24 |
| CV | 16 |

TABLE 2

Oligonucleotides for (real time) PCR[1]

PRIMERS AND PROBES FOR REAL TIME PCR

| mRNA target | Oligonucleotides (5'→3')[2] | Product size (bp) | Final concentration (nM)[3] |
|---|---|---|---|
| IL-2 | F273: CTCACCAGGATGCTCACATTTA<br>R367: TCCAGAGGTTTGAGTTCTTCTTCT<br>P304: 6FaM-TGCCCAAGAAGGCCACAGAACTG-Tamra-p | 95 | F 900<br>R 900 |
| IL-4 | F174: ACTTTGAACAGCCTCACAGAG<br>R247: TTGGAGGCAGCAAAGATGTC<br>P204: 6Fam-CTGTGCACCGAGTTGACCGTA-Tamra-p | 74 | F 300<br>R 900 |

PRIMERS FOR STANDARD PREPARATION BY "CLASSICAL" PCR[4]

| mRNA target | Oligonucleotide (5'→3')[2] | Product size (bp) |
|---|---|---|
| IL-2 | F155: TGTCACAAACAGTGCACCTACT<br>R672: AGTTACAATAGGTAGCAAACCATACA | 518 |

TABLE 2-continued

Oligonucleotides for (real time) PCR[1]

| | | |
|---|---|---|
| IL-4 | F27: TAATTGCCTCACATTGTCACT<br>R529: ATTCAGCTCGAACACTTTGAA | 503 |

[1]For a full description, see Stordeur et al, J Immunol Methods, 259(1-2): 55-64, 2002.
[2]F, R and P indicate forward and reverse primers and probes, respectively; numbers indicate the sequence position from Genebank accession numbers X01586 for IL-2 and NM_000589 for IL-4.
[3]Final concentration of forward (F) and reverse (R) primers.
[4]Standard curves were generated from serial dilution of PCR products prepared by "classical" PCR, for which specific conditions were as follows: denaturation at 95° C. for 20 s, annealing at 58° C. for 20 s and elongation at 72° C. for 45 s, for a total of 35 cycles. MgCl2 final concentration was 1.5 mM.

TABLE 3

| Tetanus Toxoid | Cord blood | Adult whole blood (before vaccine recall) |
|---|---|---|
| − | 109 ± 51 | 1,154 ± 1,194 |
| + | 159 ± 91 | 7,715 ± 8,513 |

What is claimed is:

1. A vessel suitable for accepting a liquid biological sample, which exposes said sample to a first substance and subsequently a nucleic acid stabilizing agent, said vessel comprising:
   a) a first substance present inside said vessel,
   b) a container in which said stabilizing agent is present,
   c) a connection between the inside of said vessel and the inside of said container,
   d) a physical barrier that temporarily blocks said connection,
   wherein the physical barrier of item d) is opened by the application of physical force to said vessel, and
   wherein said vessel further comprises an indication for dispensing a known volume of stabilizing agent therein.

2. The vessel according to claim 1 wherein said first substance is immobilized on part or all of the inside surface of said vessel.

3. The vessel according to claim 1 wherein said first substance is immobilized on a solid support.

4. The vessel according to claim 1 wherein said first substance is a liquid.

5. The vessel according to claim 1 wherein said first substance is a solid.

6. The vessel according to claim 1 comprising one or more areas suitable for puncture by a syringe needle.

7. The vessel according to claim 6 wherein said area is a re-sealable septum.

8. The vessel according to claim 1, further comprising a fitting suitable for receiving a syringe and transmitting the contents therein to the interior of said vessel.

9. The vessel according to claim 1, further comprising a fitting suitable for receiving a syringe needle or cannula.

10. The vessel according to claim 1, further comprising a valve which is capable of minimizing the flow of gas/liquid from the vessel, and allowing the flow of liquid biological sample into the vessel.

11. The vessel according to claim 1, further comprising a means through which displaced gas may be expelled.

12. The vessel according to claim 1 wherein said vessel is held under negative pressure.

13. The vessel according to claim 1 wherein said force transmits an opening means to said physical barrier.

14. The vessel according to claim 1 wherein said force irreversibly opens said physical barrier.

15. The vessel according to claim 1 wherein said first substance comprises one or more immune system antigens.

16. The vessel according to claim 15 wherein said immune system antigens are vaccine components.

17. The vessel according to claim 15 wherein said immune system antigens are antigens which provoke a hyperallergenic response.

18. The vessel according to claim 15 wherein said immune system antigens are one or more selected from the group consisting of histocompatibility antigens, bacterial LPS, tetanus toxoid, a cancer immunotherapy antigen, MAGE-3, a cat allergen, Feld1, antigen presenting cells from an organ donor, an autoantigen, and GAD65.

19. The vessel according to claim 1 wherein said stabilizing agent is an inhibitor of cellular RNA degradation and/or gene induction.

20. A method of testing an immune response of an individual towards an antigen comprising the steps of:
   a) introducing a sample of blood taken from said individual into the vessel of claim 1, wherein the first substance is the antigen,
   b) agitating said vessel,
   c) introducing after a pre-determined period of time, said nucleic acid stabilizing agent into said vessel, and
   d) testing the levels of mRNA thereby testing an immune response of an individual towards an antigen.

21. The method according to claim 20 where step d) further comprises the steps of:
   e) forming a precipitate comprising nucleic acids,
   f) separating said precipitate of step (e) from the supernatant,
   g) dissolving said precipitate of step (f) using a buffer, forming a suspension,
   h) isolating nucleic acids from said suspension of step (g) using an automated device,
   i) dispersing/distributing a reagent mix for RT-PCR using an automated device,
   j) dispersing/distributing the nucleic acids isolated in step (h) within the dispersed reagent mix of step (i) using an automated device, and,
   k) determining the in vivo levels of transcripts using the nucleic acid/RT-PCR reagent mix of step (j) in an automated setup.

22. The method according to claim 20 wherein the immune response of an individual towards an antigen against which the individual has been pre-immunized is tested, the first substance is the antigen under investigation and the levels of cytokine mRNA are tested.

23. The method according to claim 22 wherein said cytokine is one or more selected from the group consisting of IL-2, IL-4, IL-13, and IFN-gamma.

24. The method according to claim 20 wherein the hyperallergenicity of an individual towards an antigen is tested, the first substance is the antigen under investigation and the levels of IL-4 mRNA are tested.

25. The method according to claim 20 wherein rejection of an organ transplant in an individual towards an antigen is tested, wherein the first substance is a histocompatibility antigen of the donor and the levels of IL-2 mRNA are tested.

26. A method of testing RNA components in a stabilized blood sample comprising:
   collecting a blood sample in the vessel according to claim 1;
   pulsing a sample of blood with an antigen, subsequently inhibiting cellular RNA degradation and/or gene induction therein; and
   testing RNA components in the stabilized blood sample so pulsed.

27. A method of testing RNA components in a stabilized blood sample comprising:
   extracting a pre-determined volume sample of blood from an individual using said vessel according to claim 9;
   pulsing said sample with an antigen, subsequently inhibiting cellular RNA degradation and/or gene induction therein; and
   testing RNA components in the stabilized blood sample so pulsed.

28. A kit suitable for pulsing a liquid biological sample with a first substance, and subsequently introducing an agent that inhibits cellular RNA degradation and/or gene induction thereto, and testing mRNA components in the stabilized blood sample so pulsed, said kit comprising:
   a) a vessel in which said first substance is present, wherein said first substance comprises one or more immune system antigens, which are antigens which provoke a hyperallergenic response, and b) a container in which said agent is present, wherein the inside of said vessel and the inside of said container are connected, and a physical barrier temporarily blocks said connection that is opened by the application of physical force to said vessel.

29. The kit according to claim 28 wherein said first substance is immobilized on part or all of the inside surface of said vessel.

30. The kit according to claim 28 wherein said first substance is immobilized on a solid support.

31. The kit according to claim 28 wherein said first substance is a liquid.

32. The kit according to claim 28 wherein said first substance is a solid.

33. The kit according to claim 28 wherein said vessel comprises one or more openings.

34. The kit according to claim 28 said vessel comprises one or more areas suitable for puncture by a syringe needle.

35. The kit according to claim 34 wherein said area is a re-sealable septum.

36. The kit according to claim 28 wherein said vessel comprises one or more fittings suitable for receiving a syringe and transmitting the contents therein to the interior of said vessel.

37. The kit according to claim 28 wherein said vessel comprises one or more fittings suitable for receiving a hypodermic syringe needle.

38. The kit according to claim 28 wherein said vessel comprises one or more cannulas suitable for withdrawing bodily fluids.

39. The kit according to claim 28 wherein said vessel comprises one or more valves which are capable of minimizing the flow of liquid from the vessel, minimizing the flow of gas into or from the vessel, and/or allowing the flow of liquid biological sample into the vessel.

40. The kit according to claim 28 wherein said vessel comprises one or more means through which displaced gas may be expelled.

41. The kit according to claim 28 wherein said vessel is held under negative pressure.

42. The kit according to claim 28 wherein said force transmits an opening means to said physical barrier.

43. The kit according to claim 28 wherein said force irreversibly opens said physical barrier.

44. The kit according to claim 28 wherein said vessel and/or container comprises an indication for dispensing a known volume of stabilizing agent therein.

45. The kit according to claim 28 for testing the immune response of an individual towards an antigen against which the individual has been pre-immunized wherein the first substance is the antigen under investigation and the mRNA tested is cytokine mRNA.

46. The kit according to claim 45 wherein said cytokine is one or more selected from the group consisting of IL-2, IL-4, IL-13, and IFN-gamma.

47. The kit according to claim 28 for testing an individual for hyperallergenicity towards an antigen wherein the first substance is the antigen under investigation and the mRNA tested is IL-4 mRNA.

48. The kit according to claim 28 for testing an individual for rejection of an organ transplant wherein the first substance is a histocompatibility antigen of the donor and the mRNA tested is IL-2 mRNA.

49. The kit according to claim 28 further comprising one or more oligonucleotides suitable for said testing said mRNA(s).

50. A kit suitable for pulsing a liquid biological sample with a first substance, and subsequently introducing an agent that inhibits cellular RNA degradation and/or gene induction thereto, and testing mRNA components in the stabilized blood sample so pulsed, said kit comprising:

a) a vessel in which said first substance is present, wherein said first substance comprises one or more immune system antigens, and wherein said immune system antigens are vaccine components and b) a container in which said agent is present, wherein the inside of said vessel and the inside of said container are connected, and a physical barrier temporarily blocks said connection that is opened by the application of physical force to said vessel.

51. A kit suitable for pulsing a liquid biological sample with a first substance, and subsequently introducing an agent that inhibits cellular RNA degradation and/or gene induction thereto, and testing mRNA components in the stabilized blood sample so pulsed, said kit comprising:

a) a vessel in which said first substance is present, wherein said first substance comprises one or more immune system antigens, wherein said immune system antigens are one or more selected from the group consisting of histocompatibility antigens, bacterial LPS, tetanus toxoid, a cancer immunotherapy antigen, MAGE-3, a cat allergen, Feld1, antigen presenting cells from an organ donor, an autoantigen, and GAD65, and b) a container in which said agent is present, wherein the inside of said vessel and the inside of said container are connected, and a physical barrier temporarily blocks said connection that is opened by the application of physical force to said vessel.

* * * * *

UNITED STATES PATENT AND TRADEMARK OFFICE
CERTIFICATE OF CORRECTION

PATENT NO.       : 7,700,276 B2
APPLICATION NO.  : 10/563503
DATED            : April 20, 2010
INVENTOR(S)      : Stordeur et al.

It is certified that error appears in the above-identified patent and that said Letters Patent is hereby corrected as shown below:

Column 4, Line 35, "nucleic add stabilising" should be changed to --nucleic acid stabilising--

Column 4, Line 42, "of step (f using" should be changed to --of step (f) using--

Column 6, Line 28, "are selected from one" should be changed to --selected from one--

Column 6, Line 29, "tetanous toxoid," should be changed to --tetanus toxoid,--

Column 7, Line 13, "the RNAlater reagent" should be changed to --the RNA later reagent--

Column 7, Line 17, NaCI alone or an" should be changed to --NaCl alone or an--

Column 8, Line 61, "I.42-43). Therefore," should be changed to --1.42-43). Therefore,--

Column 11, Line 14, "is tetanous toxoid." should be changed to --is tetanus toxoid.--

Column 18, Line 59, "directly of indirectly" should be changed to --directly or indirectly--

Column 19, Line 2, "with an identical similar" should be changed to --with an identical/similar--

Column 19, Line 53, "the pulsed/nonpulsed cells," should be changed to --the pulsed/non-pulsed cells,--

Column 26, Line 8, "the same individual," should be changed to --the same individuals,--

Column 26, Line 32, "tetradecyltrirmethylammonium oxalate" should be changed to --tetradecyltrimethylammonium oxalate--

Column 29, Line 21, "(dendritc cells," should be changed to --(dendritic cells,--

Column 29, Line 64, "epitope-specifiq CTLs" should be changed to --epitope-specific CTLs--

Column 30, Line 44, "is damaged Would" should be changed to --is damaged would--

Column 30, Line 48, "subclinical episodes of" should be changed to --sub-clinical episodes of--

Column 31, Line 15, "Pure™0 instrument" should be changed to -- Pure™ instrument--

Signed and Sealed this

Seventh Day of September, 2010

David J. Kappos
*Director of the United States Patent and Trademark Office*

Column 31, Line 45, "of the PAXgene™0 tube's" should be changed to --of the PAXgene™ tube's--

Column 33, Line 25, "and IFNγ mRNAs" should be changed to --and IFN-γ mRNAs--

Column 35, Line 9, "quantfication errors," should be changed to --quantification errors,--

Column 35, Line 64, "in vitro incubaton" should be changed to --in vitro incubation--

Column 36, Line 25, "to monitor alloreactve" should be changed to --to monitor alloreactive--

Column 37, Line 14, "6FaM-" should be changed to --6Fam- --

Column 38, Lines 15-16, "dilution of PCR" should be changed to --dilutions of PCR--